(12) United States Patent
Kawasaki et al.

(10) Patent No.: US 9,949,982 B2
(45) Date of Patent: Apr. 24, 2018

(54) PREPARATION CONTAINING CEPHALOSPORIN HAVING A CATECHOL MOIETY

(71) Applicant: Shionogi & Co., Ltd., Osaka (JP)

(72) Inventors: Hidenori Kawasaki, Osaka (JP); Natsuko Kojima, Osaka (JP); Atsushi Fujihira, Osaka (JP); Kanako Takahashi, Osaka (JP); Fumihiko Matsubara, Osaka (JP); Nao Matsuoka, Osaka (JP)

(73) Assignee: Shionogi & Co., Ltd., Osaka (JP)

( * ) Notice: Subject to any disclaimer, the term of this patent is extended or adjusted under 35 U.S.C. 154(b) by 0 days.

(21) Appl. No.: 15/508,406

(22) PCT Filed: Sep. 3, 2015

(86) PCT No.: PCT/JP2015/075040
§ 371 (c)(1),
(2) Date: Mar. 2, 2017

(87) PCT Pub. No.: WO2016/035846
PCT Pub. Date: Mar. 10, 2016

(65) Prior Publication Data
US 2017/0281639 A1    Oct. 5, 2017

(30) Foreign Application Priority Data

Sep. 4, 2014 (JP) .................................. 2014-180174

(51) Int. Cl.
| | |
|---|---|
| A61K 31/546 | (2006.01) |
| A61K 47/02 | (2006.01) |
| A61K 47/26 | (2006.01) |
| A61K 47/20 | (2006.01) |
| A61K 9/19 | (2006.01) |
| A61K 9/00 | (2006.01) |

(52) U.S. Cl.
CPC .......... *A61K 31/546* (2013.01); *A61K 9/0019* (2013.01); *A61K 9/19* (2013.01); *A61K 47/02* (2013.01); *A61K 47/20* (2013.01); *A61K 47/26* (2013.01)

(58) Field of Classification Search
CPC ................................................... A61K 31/546
USPC ........................................................ 544/47
See application file for complete search history.

(56) References Cited

U.S. PATENT DOCUMENTS

| 4,616,083 A | 10/1986 | Shima et al. |
| 5,254,545 A | 10/1993 | Ishibashi et al. |
| 2011/0190254 A1 | 8/2011 | Nishitani et al. |

FOREIGN PATENT DOCUMENTS

| CA | 2293008 | 12/1999 |
|---|---|---|
| EP | 134568 | 8/1983 |
| EP | 253329 | 1/1988 |
| EP | 325112 | 7/1989 |
| EP | 421297 | 10/1991 |
| EP | 2341053 | 7/2011 |
| GB | 2199746 | 7/1988 |
| JP | 58-113125 | 7/1983 |
| JP | 60-45514 | 3/1985 |
| JP | 63-17827 | 1/1988 |
| JP | 63-208522 | 8/1988 |
| JP | 1-216996 | 8/1989 |
| JP | 3-173822 | 7/1991 |
| JP | 3-264531 | 11/1991 |
| JP | 4-59730 | 2/1992 |
| JP | 6-122630 | 5/1994 |
| JP | 7-082149 | 3/1995 |
| JP | 2000219628 | 8/2000 |
| JP | 2004269401 | 9/2004 |
| JP | 2009286738 | 12/2009 |
| JP | 2001316266 | 11/2011 |
| WO | 2010050468 | 5/2010 |

OTHER PUBLICATIONS

Ashizawa et al.: "Solid-State Stability and Preformulation Study of a New Parenteral Cephalosporin Antibiotics"; Tsukuba Research Laboratories, Pharmaceutical Society of Japan, 1989, pp. 191-201, English summary.

(Continued)

*Primary Examiner* — Kahsay Habte
(74) *Attorney, Agent, or Firm* — Hamre, Schumann, Mueller & Larson, P.C.

(57) ABSTRACT

The present invention relates to a stable pharmaceutical composition comprising a compound represented by formula (I), its pharmaceutically acceptable salt or a solvate thereof.

(I)

The stable pharmaceutical composition can be prepared by comprising 1) a compound represented by formula (I), its pharmaceutically acceptable salt, or a solvate thereof, 2) one or more selected from the group consisting of alkali metal chlorides, alkaline earth metal chlorides, transition metal chlorides and magnesium chloride; and 3) sugar and/or a sugar alcohol.

36 Claims, No Drawings

(56) References Cited

OTHER PUBLICATIONS

International Search Report issued in International Application No. PCT/JP2015/075040 dated Oct. 6, 2015 (5 pages).
Written Opinion issued in International Application No. PCT/JP2015/075040 dated Oct. 6, 2015 (5 pages).

PREPARATION CONTAINING CEPHALOSPORIN HAVING A CATECHOL MOIETY

TECHNICAL FIELD

The pharmaceutical preparation of the present invention relates to a stable pharmaceutical preparation comprising the cephem compound, which has strong antibacterial activity especially, to grain negative bacteria producing β-lactamase.

BACKGROUND ART

Various β-lactam medicines have been developed until now, and β-lactam medicines are very important antibacterial medicines clinically. However, the bacterial strains which have acquired tolerance to β-lactam medicines by producing β-lactamase are increased. The compound represented by the following formula (I), its pharmaceutically acceptable salt or solvate thereof was discovered as an agent to exhibiting strong antibacterial spectrum against several bacteria including gram negative bacteria and/or gram positive bacteria, and the above problem was solved (Patent Document 1).

Formula (I):

[Chemical formula 1]

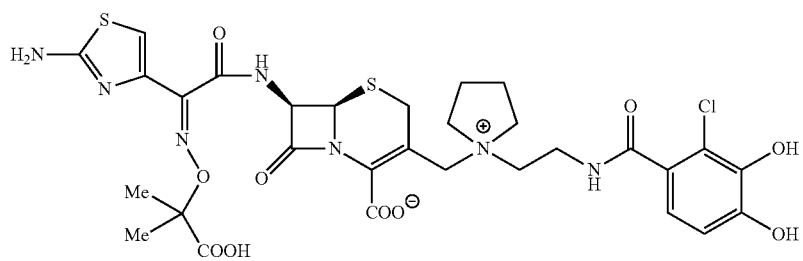

(I)

However, when temporal stability test was performed on the compound represented by formula (I), its pharmaceutically acceptable salt or solvate thereof, it was found that the analogue of the compound is produced and the residual ratio of the compound (I) decreased.

As examples of the pharmaceutical preparation which stabilizes an antibiotic such as a cephem compound, the pharmaceutical preparation containing lactose and sodium chloride as an additive (Patent Document 2), the pharmaceutical preparation containing lactose, sodium chloride and citrate (Patent Document 3), the pharmaceutical preparation containing glucose (Patent Documents 4 and 5), the pharmaceutical preparation containing one or more selected from glucose, fructose and maltose, and alkali metal salt (Patent Document 6), the pharmaceutical preparation containing halogenide (Patent Documents 7), the pharmaceutical preparation containing maltose and sodium chloride (Patent Documents 8), the pharmaceutical preparation containing the salt, the cation of the salt is one or more selected from one or more selected from the group consisting of sodium, calcium and magnesium, the anion of the salt is one or more selected from the group consisting of chloride, fluoride and iodide (Patent Document 9) and the pharmaceutical preparation containing sodium chloride and sucrose (Non-Patent Document 1) are disclosed. However, the pharmaceutical preparation capable of satisfying stability for the compound represented by above formula (I), its pharmaceutically acceptable salt or solvate thereof cannot be prepared by these documents.

As examples of the stable injectable preparation, the pharmaceutical preparation containing alatrofloxacin as an antibiotic, sodium chloride and sucrose, and the like (Patent Document 10), and the pharmaceutical preparation containing nicardipine hydrochloride as an active ingredient, sodium gluconate, and sodium chloride (Patent Document 11) are disclosed. However, there are great differences on the chemical structure among alatrofloxacin, nicardipine hydrochloride and the compound represented by formula (I), its pharmaceutically acceptable salt or solvate thereof, and these documents cannot contribute the stability of the compound represented by above formula (I), its pharmaceutically acceptable salt or solvate thereof.

PRIOR ART

Patent Document

Patent Document 1: International publication pamphlet WO2010/050468
Patent Document 2: JP-A No. 63-17827
Patent Document 3: JP A No. 3-173822
Patent Document 4: JP A No. 58-113125
Patent Document 5: JP A No. 7-82149
Patent Document 6: JP A No. 60-45514
Patent Document 7: JP A No. 2004-269401
Patent Document 8: JP A No. 2009-286738
Patent Document 9: JP A No. 63-208522
Patent Documents 10: JP A No. 2000-219628
Patent Documents 11: JP A No. 2001-318266
Non-Patent Document 1: Yakugakuzasshi Vol. 110, No. 3 Page 191-201 (1990)

DISCLOSURE OF INVENTION

Problems to be Solved by the Invention

Therefore, a stable preparation comprising the compound represented by the above formula (I), its pharmaceutically acceptable salt or solvate thereof has been desired.

Means to Solve the Problems

The present inventors intensively studied, and found out that the pharmaceutical preparation having improved temporal stability can be prepared, that is, the pharmaceutical preparation which comprising 1) the compound represented by formula (I), its pharmaceutically acceptable salt or solvate thereof, preferably, its sodium salt represented by formula (II), 2) one or more selected from the group consisting of alkali metal chloride, alkali earth metal chloride, transition metal chloride and magnesium chloride, and 3) sugar and/or sugar alcohol (hereafter, "The pharmaceutical preparation of the present invention").

That is, the present invention includes:

(1) A pharmaceutical composition characterized by comprising at least the following components:
1) a compound of formula (I):

[Chemical formula 2]

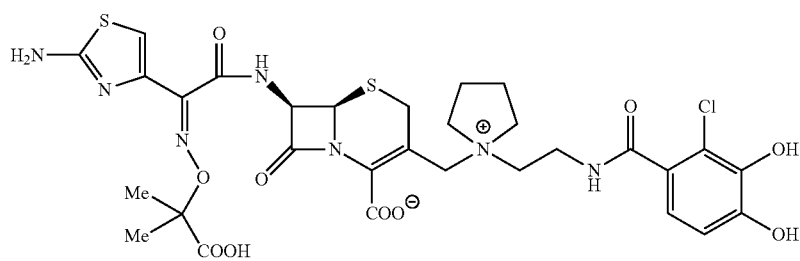

(I)

its pharmaceutically acceptable salt or solvate thereof,
2) one or more selected from the group consisting of alkali metal chloride, alkali earth metal chloride, transition metal chloride and magnesium chloride, and
3) sugar and/or sugar alcohol, (2) the pharmaceutical composition according to the above (1), wherein said component 1) is sodium salt of the compound represented by formula (II):

[Chemical formula 3]

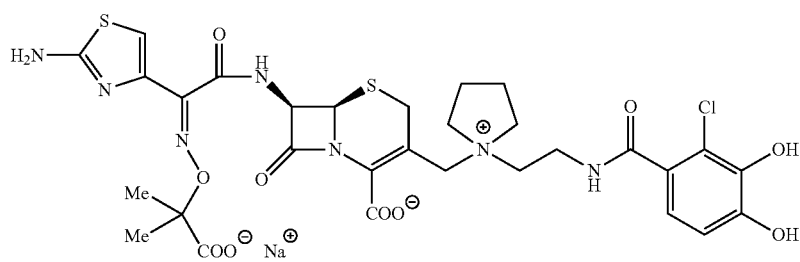

(II)

(3) the pharmaceutical composition according to the above (1) or (2), wherein said, component 1) is amorphous, (4) the pharmaceutical composition according to any one of the above (1) to (3), which further comprises alkali metal salt, alkali earth metal salt, transition metal chloride or magnesium chloride of an organic acid or inorganic acid, or its hydrate, (5) the pharmaceutical composition according to the above (4), wherein said acid is one or more selected from the group consisting of p-toluenesulfonic acid, benzenesulfonic acid, sulfuric acid, hydrochloric acid and hydrobromic acid, (6) the pharmaceutical composition according to the above (4), wherein said acid is p-toluenesulfonic acid and/or sulfuric acid, (7) the pharmaceutical composition according to any one of the above (4) to (6), wherein said salt is sodium salt, (8) the pharmaceutical composition according to any one of the above (1) to (7), which comprises alkali metal chloride, wherein said alkali metal chloride is sodium chloride or potassium chloride, (9) the pharmaceutical composition according to the above (8), which comprises alkali metal chloride, wherein said alkali metal chloride is sodium chloride,

(10) the pharmaceutical composition according to any one of the above (1) to (7), which comprises alkali earth metal chloride, wherein said alkali earth metal chloride is calcium chloride,

(11) the pharmaceutical composition according to any one of the above (1) to (7), which comprises transition metal chloride, wherein said transition metal chloride is zinc chloride,

(12) the pharmaceutical composition according to any one of the above (1) to (11), wherein said sugar or sugar alcohol is one or more selected from the group consisting of monosaccharide, disaccharide and polysaccharide,

(13) the pharmaceutical composition according to the above (12), wherein said sugar or sugar alcohol is one or more selected from the group consisting of glucose, fructose, sucrose, mannitol and trehalose,

(14) the pharmaceutical composition according to the above (12), which comprises sugar or sugar alcohol, wherein said sugar or sugar alcohol is sucrose,

(15) the pharmaceutical composition according to any one of the above (1) to (14), which comprises alkali metal chloride, and sugar or sugar alcohol, wherein said alkali metal chloride is sodium chloride, and said sugar or sugar alcohol is sucrose.

(16) the pharmaceutical composition according to the above (15), which comprises sodium chloride of 0.7 to 5.0 mole equivalent as alkali metal chloride, and sucrose of 0.3 to 4.0 mole equivalent as sugar or sugar alcohol, to said component 1),

(17) the pharmaceutical composition according to the above (16), which further comprises alkali metal salt of p-toluenesulfonic acid of 0.25 to 2.5 mole equivalent, and alkali metal salt of sulfuric acid of 0.05 to 2.0 mole equivalent, to said component 1),

(18) the pharmaceutical composition according to the above (15), which comprises sodium chloride of 0.7 to 5.0 mole equivalent as alkali metal chloride, and sucrose of 0.3 to 4.0 mole equivalent as sugar or sugar alcohol, to the sodium salt of said component 1),

(19) the pharmaceutical composition according to the above (18), which further comprises sodium p-toluenesulfonate of 0.25 to 2.5 mole equivalent, and sodium sulphate of 0.05 to 2.0 mole equivalent, to the sodium salt of said component 1),

(20) the pharmaceutical composition according to any one of the above (16) to (19), wherein the increased amount of the compound represented by formula (III):

[Chemical formula 4]

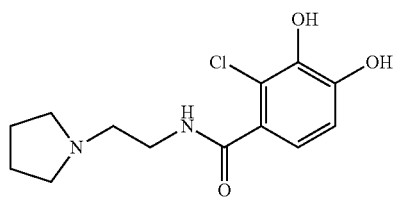

(III)

in said pharmaceutical composition is less than 0.4% from the start of storage under 40° C. for two weeks storage.

(21) the pharmaceutical composition according to any one of the above (16) to (19), wherein the increased amount of the compound represented by formula (III) in said pharmaceutical composition is less than 0.05% from the start of storage under 25° C. for two weeks storage,

(22) the pharmaceutical composition according to any one of the above (16) to (19), wherein the increased amount of the compound represented by formula (IV):

[Chemical formula 5]

in said pharmaceutical composition is less than 0.05% from the start of storage under 25° C. for two weeks storage,

(23) the pharmaceutical composition according to any one of the above (16) to (19), wherein the increased amount of the compound represented by formula (III) in said pharmaceutical composition is less than 0.05%, and the increased amount of the compound represented by formula (IV) in said pharmaceutical composition is less than 0.05%,

(24) the pharmaceutical composition according to any one of the above (1) to (23), which further comprises sodium gluconate,

(25) the pharmaceutical composition comprising the component 1), wherein the increased amount of the compound represented by formula (III):

[Chemical formula 6]

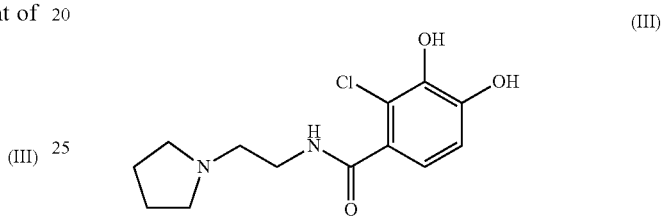

(III)

in said pharmaceutical composition is less than 0.4% from the start of storage under 40° C. for two weeks storage (the component 1) is the same meaning in the above (1).),

(26) the pharmaceutical composition comprising the component 1), wherein the increased amount of the compound represented by formula (III) in said pharmaceutical composition is less than 0.05% from the start of storage under 25° C. for two weeks storage (the component 1) is the same meaning in the above (1).),

(27) the pharmaceutical composition comprising the component 1) wherein the increased amount of the compound represented by formula (IV):

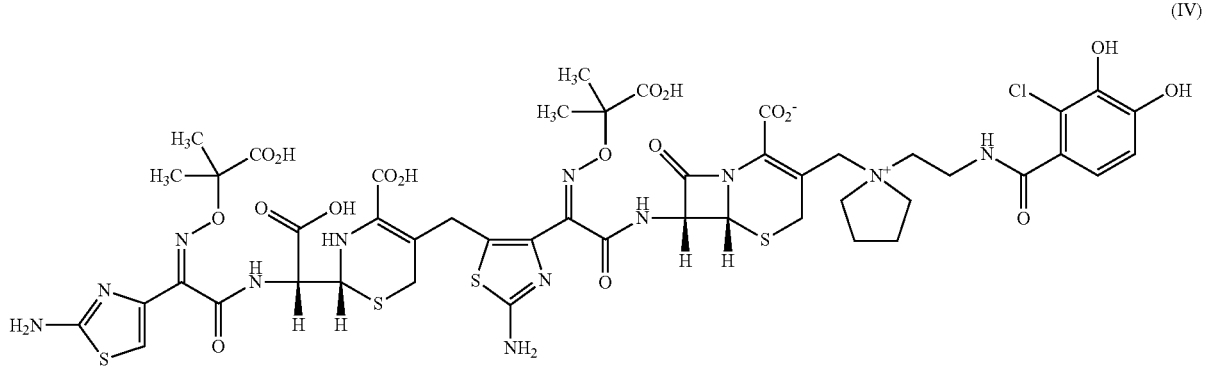

(IV)

[Chemical formula 7]

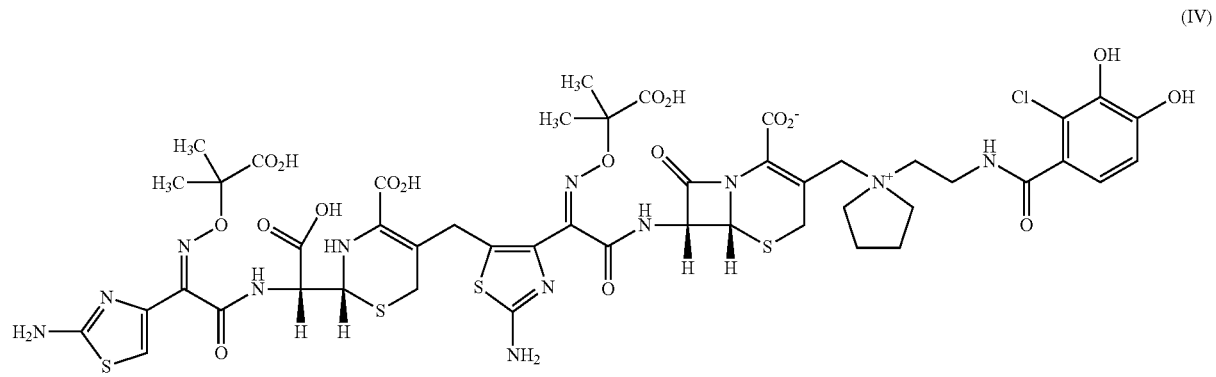

in said pharmaceutical composition is less than 0.05% from the start of storage under 25° C. for two weeks storage (the component 1) is the same meaning in the above (1).),

(28) the pharmaceutical composition comprising the component 1), wherein the increased amount of the compound represented by formula (III) in said pharmaceutical composition is less than 0.05%, and the increased amount of the compound represented by formula (IV) in said pharmaceutical composition is less than 0.05% from the start of storage under 25° C. for two weeks storage (the component 1) is the same meaning in the above (1).),

(29) the pharmaceutical composition according to any one of the above (1) to (28).), which is a lyophilized product,

(30) the pharmaceutical composition according to any one of the above (1) to (29), which is an injection,

(31) a manufacturing method of the pharmaceutical preparation which comprises at least the following steps (the components 2) and 3) are the same meanings in the above (1).):

a) a step of adjusting the liquid comprising the compound represented by formula (I), its pharmaceutically acceptable salt or solvate thereof:

to pH 5 to 6 by alkali materials, b) a step of mixing the liquid which is prepared by said step a), said component 2) and said component 3), and c) a step of lyophilizing the mixture prepared by said step b),

(32) the manufacturing method of the pharmaceutical preparation which comprise at least the following steps:

a) the step of adjusting the suspension comprising the compound represented by formula (I), its pharmaceutically acceptable salt or solvate thereof to pH 5 to 6 by sodium hydroxide, b) the step of mixing the liquid which is prepared by said step a), said component 2) and said component 3), and c) the step of lyophilizing the mixture prepared by said step b),

(33) The pharmaceutical composition prepared by the manufacturing method of the pharmaceutical preparation according to the above (31) or (32).

Effect of the Invention

When the temporal stability test of the pharmaceutical preparation of the present invention was conducted, the stability of the compound represented by the following formula (I), its pharmaceutically acceptable salt or solvate thereof was found to be improved.

[Chemical formula 8]

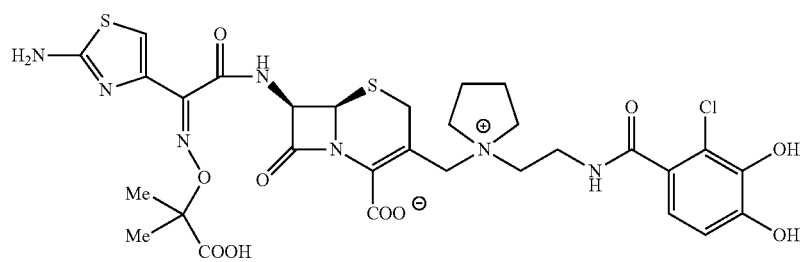

BEST MODE FOR CARRYING OUT THE INVENTION

In the specification, the active ingredient in the pharmaceutical preparation of the present invention is represented by formula (I):

[Chemical formula 9]
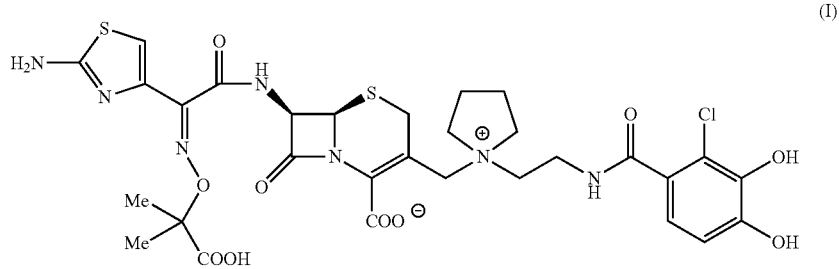
(I)
But the compound substantially can also become the state on the compound of formula (I').
[Chemical formula 10]
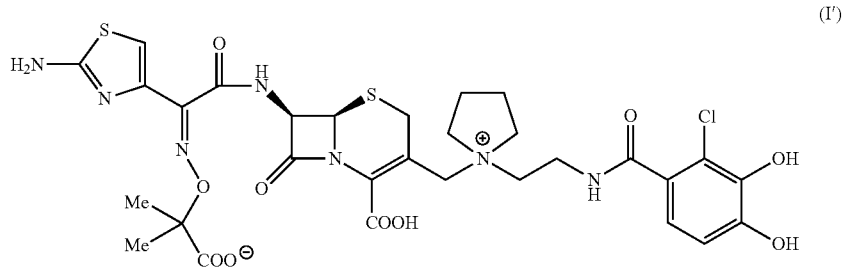
(I')
so the compounds of the both chemical structures are included in the present invention. The sodium salt of the compound represented by formula (I) includes
[Chemical formula 11]
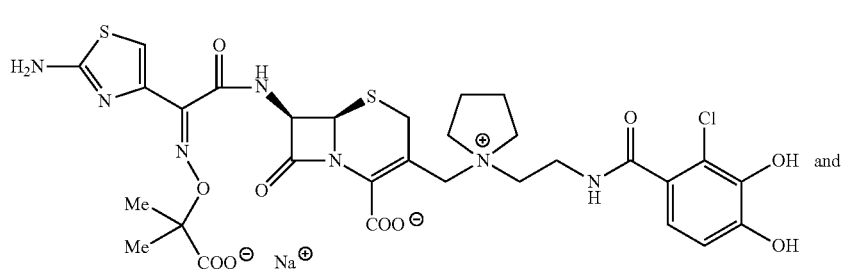
(II)
and
[Chemical formula 12]
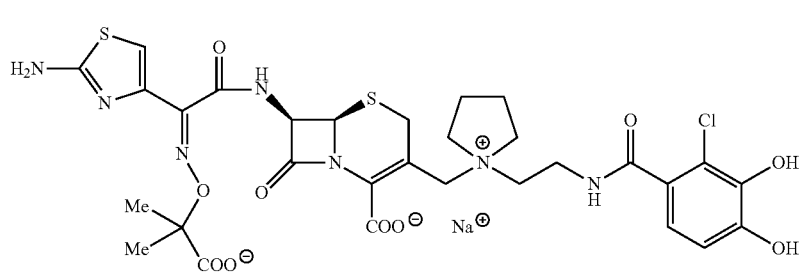
(II')

The compound represented by formula (I), its pharmaceutically acceptable salt or solvate thereof, and the sodium salt represented by formula (II) may be amorphous (non-crystalline). Moreover, the molecular weight of the compound represented by formula (I) is 752.21 and that of the sodium salt of the compound represented by formula (II) is 774.20.

The pharmaceutical preparation of the present invention comprises one or more selected from the group consisting of alkali metal chloride, alkali earth metal chloride, transition metal chloride and magnesium chloride, and sugar and/or sugar alcohol to stabilize the compound represented by formula (I), its pharmaceutically acceptable salt or solvate thereof and the sodium salt of the compound represented by formula (II).

As alkali metal chloride, those stabilize the compound represented by formula (I), its pharmaceutically acceptable salt or solvate thereof and the sodium salt of the compound represented by formula (II), and described in Japanese Pharmacopoeia, Pharmaceutical Standards outside the Japanese Pharmacopoeia, Japanese Pharmaceutical Excipients and Japanese Standard of Food Additives may be used. Examples of alkali metal chloride include sodium chloride, lithium chloride, potassium chloride and the like, preferably sodium chloride.

As alkali earth metal chloride, those stabilize the compound represented by formula (I), its pharmaceutically acceptable salt or solvate thereof and the sodium salt of the compound represented by formula (II), and described in Japanese Pharmacopoeia, Pharmaceutical Standards outside the Japanese Pharmacopoeia, Japanese Pharmaceutical Excipients and Japanese Standard of Food Additives may be used. Examples of alkali earth metal chloride include barium chloride, calcium chloride and the like, preferably calcium chloride.

As transition metal chloride, those stabilize the compound represented by formula (I), its pharmaceutically acceptable salt or solvate thereof and the sodium salt of the compound represented by formula (II), and described in Japanese Pharmacopoeia, Pharmaceutical Standards outside the Japanese Pharmacopoeia, Japanese Pharmaceutical Excipients and Japanese Standard of Food Additives may be used. Examples of transition metal chloride include chromium chloride and zinc chloride and the like, preferably zinc chloride.

Moreover, magnesium chloride may be used to stabilize the compound represented by formula (I), its pharmaceutically acceptable salt or solvate thereof and the sodium salt of the compound represented by formula (II). As magnesium chloride, those described in Japanese Pharmacopoeia, Pharmaceutical Standards outside the Japanese Pharmacopoeia, Japanese Pharmaceutical Excipients and Japanese Standard of Food Additives may be used.

As sugar and/or sugar alcohol, those stabilize the compound represented by formula (I), its pharmaceutically acceptable salt or solvate thereof and the sodium salt of the compound represented by formula (II), and described in Japanese Pharmacopoeia, Pharmaceutical Standards outside the Japanese Pharmacopoeia, Japanese Pharmaceutical Excipients and Japanese Standard of Food Additives may be used. Examples of sugar and/or sugar alcohol include monosaccharide, disaccharide and polysaccharide, preferably glucose, fructose, sucrose, mannitol, trehalose, and the like, more preferably sucrose.

Moreover, to stabilize the compound represented by formula (I), its pharmaceutically acceptable salt or solvate thereof and the sodium salt of the compound represented by formula (II), alkali metal salt, alkali earth metal salt, transition metal chloride or magnesium salt of organic acid or inorganic acid or its hydrate may be used.

Examples of said organic acid or inorganic acid include p-toluene sulfonic acid, benzene sulfonic acid, sulfuric acid, hydrochloric acid and hydrobromic acid, preferably p-toluene sulfonate, sulfuric acid.

Examples of said alkali metal salt, alkali earth metal salt, transition metal chloride or magnesium salt of organic acid or inorganic acid or its hydrate include sodium salt, lithium salt, potassium salt, calcium salt, zinc salt magnesium salt, and the like, preferably sodium salt, magnesium salt, more preferably sodium salt. Examples of more preferable salt include sodium p-toluene sulfonate, magnesium p-toluene sulfonate, sodium sulfate, magnesium sulfate. Examples of especially preferable salt include sodium p-toluene sulfonate and sodium sulfate.

The pharmaceutical preparation may comprise the anti-oxidized agent, buffer agent, soothing agent, preserving agent, and the like which can be used by the injection except those mentioned above, if necessary, those to stabilize the compound represented by formula (I), its pharmaceutically acceptable salt or solvate thereof and the sodium salt of the compound represented by formula (II), described in Japanese Pharmacopoeia, Pharmaceutical Standards outside the Japanese Pharmacopoeia, Japanese Pharmaceutical Excipients and Japanese Standard of Food Additives. Examples of anti-oxidized agent include sodium hydrogen sulfite, sodium pyrosulfife, ascorbic acid, and the like. Examples of buffer agent include citric acid salt, acetic acid salt, phosphate acid salt, and the like. Examples of soothing agent include procaine hydrochloride, lidocaine hydrochloride, chlorobutanol, benzyl alcohol, and the like. Examples of preserving agent include methyl parahydroxybenzoate, propyl parahydroxybenzoate, phenol, crezol, benzyl alcohol, chlorobutanol, chlorocrezol, and the like.

As the combination of one or more selected from the group consisting of alkali metal chloride, alkali earth metal chloride, transition metal chloride and magnesium chloride, and sugar and/or sugar alcohol, those stabilize the compound represented by formula (I), its pharmaceutically acceptable salt or solvate thereof and the sodium salt of the compound represented by formula (II) may be used.

Examples of these combinations include a) the compound represented by formula (I), its pharmaceutically acceptable salt or solvate thereof, sodium chloride, sucrose, b) the sodium salt of the compound represented by formula (II), sodium chloride, sucrose, c) the compound represented by formula (I), its pharmaceutically acceptable salt or solvate thereof, magnesium chloride, sucrose, d) the sodium salt of the compound represented by formula (II), magnesium chloride, sucrose, preferably, a), b), more preferably, b).

When the pharmaceutical preparation comprises sodium chloride as alkali metal chloride and sucrose as sugar and/or sugar alcohol to the compound represented by formula (I), its pharmaceutically acceptable salt or solvate thereof, a content of sodium chloride is 0.7 to 5.0 molar equivalent, sucrose is 0.3 to 4.0 molar equivalent, preferably, the content of sodium chloride is 1.25 to 4.5 molar equivalent, sucrose is 0.75 to 3.5 molar equivalent, more preferably, the content of sodium chloride is 1.5 to 4.0 molar equivalent, sucrose is 1.0 to 3.0 molar equivalent.

When the pharmaceutical preparation comprises sodium chloride as alkali metal chloride and sucrose as sugar and/or sugar alcohol to sodium salt of the compound represented by formula (II), a content of sodium chloride is 0.7 to 5.0 molar equivalent, sucrose is 0.3 to 4.0 molar equivalent, preferably, the content of sodium chloride is 1.25 to 4.5 molar equivalent, sucrose is 0.75 to 3.5 molar equivalent, more preferably, the content of sodium chloride is 1.5 to 4.0 molar equivalent, sucrose is 1.0 to 3.0 molar equivalent.

As the combination of one or more selected from the group consisting of alkali metal chloride, alkali earth metal chloride, transition metal chloride and magnesium chloride, sugar and/or sugar alcohol, and alkali metal salt, alkali earth metal salt, transition metal chloride or magnesium salt or its hydrate of organic acid or inorganic acid, those stabilize the compound represented by formula (I), its pharmaceutically acceptable salt or solvate thereof and the sodium salt of the compound represented by formula (II) may be used.

Examples of these combinations include a) the compound represented by formula (I), its pharmaceutically acceptable acid additive salt or solvate thereof, sodium chloride, sucrose and alkali metal salt of p-toluene sulfonate, b) the compound represented by formula (I), its pharmaceutically acceptable acid additive salt or a solvate thereof, sodium chloride, sucrose and alkali metal salt of sulfuric acid, c) the compound represented by formula (I), its pharmaceutically acceptable acid additive salt or a solvate thereof, sodium chloride, sucrose, alkali metal salt of p-toluene sulfonate and alkali metal salt of sulfuric acid, d) sodium salt of the compound represented by formula (II), sodium chloride, sucrose and alkali metal salt of p-toluene sulfonate, e) sodium salt of the compound represented by formula (II), sodium chloride, sucrose and alkali metal salt of sulfuric acid, f) sodium salt of the compound represented by formula (II), sodium chloride, sucrose, alkali metal salt of p-toluene sulfonate and alkali metal salt of sulfuric acid, g) the compound represented by formula (I), its pharmaceutically acceptable acid additive salt or a solvate thereof, magnesium chloride, sucrose and alkali metal salt of p-toluene sulfonate, h) the compound represented by formula (I), its pharmaceutically acceptable acid additive salt or a solvate thereof, magnesium chloride, sucrose and alkali metal salt of sulfuric acid, i) the compound represented by formula (I), its pharmaceutically acceptable acid additive salt or a solvate thereof, magnesium chloride, sucrose and alkali metal salt of p-toluene sulfonate, j) sodium salt of the compound represented by formula (II), magnesium chloride, sucrose and alkali metal salt of p-toluene sulfonate, k) sodium salt of the compound represented by formula (II), magnesium chloride, sucrose and alkali metal salt of sulfuric acid, l) sodium salt of the compound represented by formula (II), magnesium chloride, sucrose and alkali metal salt of p-toluene sulfonate. Preferably, c), f), and more preferably, f).

When the pharmaceutical preparation comprises sodium chloride as alkali metal chloride, sucrose as sugar and/or sugar alcohol, alkali metal salt of p-toluene sulfonate and alkali metal salt of sulfuric add to the compound represented by formula (I), its pharmaceutically acceptable salt or solvate thereof, a content of sodium chloride is 0.7 to 5.0 molar equivalent, sucrose is 0.3 to 4.0 molar equivalent, alkali metal salt of p-toluene sulfonate is 0.25 to 2.5 molar equivalent and alkali metal salt of sulfuric acid is 0.025 to 2.0 molar equivalent, preferably, the content of sodium chloride is 1.25 to 4.5 molar equivalent, sucrose is 0.5 to 4.0 molar equivalent, alkali metal salt of p-toluene sulfonate is 0.5 to 2.25 molar equivalent and alkali metal salt of sulfuric acid is 0.075 to 1.5 molar equivalent, more preferably, a content of sodium chloride is 1.5 to 4.0 molar equivalent, sucrose is 1.0 to 3.0 molar equivalent, alkali metal salt of p-toluene sulfonate is 0.75 to 2.0 molar equivalent and alkali metal salt of sulfuric acid is 0.1 to 1.0 molar equivalent.

When the pharmaceutical preparation comprises sodium chloride as alkali metal chloride, sucrose as sugar and/or sugar alcohol, alkali metal salt of p-toluene sulfonate and alkali metal salt of sulfuric acid to the sodium salt of the compound represented by formula (II), a content of sodium chloride is 0.7 to 5.0 molar equivalent, sucrose is 0.3 to 4.0 molar equivalent, alkali metal salt of p-toluene sulfonate is 0.25 to 2.5 molar equivalent and alkali metal salt of sulfuric acid is 0.025 to 2.0 molar equivalent, preferably, the content of sodium chloride is 1.25 to 4.5 molar equivalent, sucrose is 0.5 to 4.0 molar equivalent, alkali metal salt of p-toluene sulfonate is 0.5 to 2.25 molar equivalent and alkali metal salt of sulfuric acid is 0.075 to 1.5 molar equivalent, more preferably, a content of sodium chloride is 1.5 to 4.0 molar equivalent, sucrose is 1.0 to 3.0 molar equivalent, alkali metal salt of p-toluene sulfonate is 0.75 to 2.0 molar equivalent and alkali metal salt of sulfuric acid is 0.1 to 1.0 molar equivalent.

As the combination of one or more selected from the group consisting of alkali metal chloride, alkali earth metal chloride, transition metal chloride and magnesium chloride, sugar and/or sugar alcohol, and alkali metal salt, alkali earth metal salt, transition metal chloride or magnesium salt or its hydrate of organic acid or inorganic acid, those stabilize the compound represented by formula (I), its pharmaceutically acceptable salt or solvate thereof and the sodium salt of the compound represented by formula (II) may be used.

Examples of these combinations include a) the compound represented by formula (I), its pharmaceutically acceptable acid additive salt or a solvate thereof, sodium chloride, sucrose and sodium p-toluene sulfonate, b) the compound represented by formula (I), its pharmaceutically acceptable acid additive salt or a solvate thereof, sodium chloride, sucrose and sodium, sulfate, c) the compound represented by formula (I), its pharmaceutically acceptable acid additive salt or a solvate thereof, sodium chloride, sucrose, sodium p-toluene sulfonate and sodium sulfate, d) sodium salt of the compound represented by formula (II), sodium chloride, sucrose and sodium p-toluene sulfonate, e) sodium salt of the compound represented by formula (II), sodium chloride, sucrose and sodium sulfate, f) sodium salt of the compound represented by formula (II), sodium chloride, sucrose, sodium p-toluene sulfonate and sodium sulfate, g) the compound represented by formula (I), its pharmaceutically acceptable acid additive salt or a solvate thereof, magnesium chloride, sucrose and sodium p-toluene sulfonate, h) the compound represented by formula (I), its pharmaceutically acceptable acid additive salt or a solvate thereof, magnesium chloride, sucrose and sodium sulfate, i) the compound represented by formula (I), its pharmaceutically acceptable acid additive salt or a solvate thereof, magnesium chloride, sucrose, sodium p-toluene sulfonate and sodium sulfate, j) sodium salt of the compound represented by formula (II), magnesium chloride, sucrose and sodium p-toluene sulfonate, k) sodium salt of the compound represented by formula (II), magnesium chloride, sucrose and sodium sulfate, l) sodium salt of the compound represented by formula (II), magnesium chloride, sucrose, sodium p-toluene sulfonate and sodium sulfate. Preferably, c), f), and more preferably, f).

When the pharmaceutical preparation comprises sodium chloride as alkali metal chloride, sucrose as sugar and/or sugar alcohol, sodium p-toluene sulfonate as alkali metal salt of p-toluene sulfonate and sodium sulfate as alkali metal salt of sulfuric acid to the compound represented by formula (I), its pharmaceutically acceptable salt or solvate thereof, a content of sodium chloride is 0.7 to 5.0 molar equivalent, sucrose is 0.3 to 4.0 molar equivalent, sodium p-toluene sulfonate is 0.25 to 2.5 molar equivalent and sodium sulfate is 0.025 to 2.0 molar equivalent, preferably the content of sodium chloride is 1.25 to 4.5 molar equivalent, sucrose is 0.5 to 4.0 molar equivalent, sodium p-toluene sulfonate is 0.5 to 2.25 molar equivalent and sodium sulfate is 0.075 to 1.5 molar equivalent, more preferably, a content of sodium chloride is 1.5 to 4.0 molar equivalent, sucrose is 1.0 to 3.0 molar equivalent, sodium p-toluene sulfonate is 0.75 to 2.0 molar equivalent and sodium sulfate is 0.1 to 1.0 molar equivalent.

When the pharmaceutical preparation comprises sodium chloride as alkali metal chloride, sucrose as sugar and/or sugar alcohol, sodium p-toluene sulfonate and sodium sulfate to the sodium salt of the compound represented by formula (II), a content of sodium chloride is 0.7 to 5.0 molar equivalent, sucrose is 0.3 to 4.0 molar equivalent, sodium p-toluene sulfonate is 0.25 to 2.5 molar equivalent and sodium sulfate is 0.025 to 2.0 molar equivalent, preferably, the content of sodium chloride is 1.25 to 4.5 molar equivalent, sucrose is 0.5 to 4.0 molar equivalent, sodium p-toluene sulfonate is 0.5 to 2.25 molar equivalent and sodium sulfate is 0.075 to 1.5 molar equivalent, more preferably, a content of sodium chloride is 1.5 to 4.0 molar equivalent, sucrose is 1.0 to 3.0 molar equivalent, sodium p-toluene sulfonate is 0.75 to 2.0 molar equivalent and sodium sulfate is 0.1 to 1.0 molar equivalent.

Moreover, sodium gluconate as an additive may be contented.

As the combination of one or more selected from the group consisting of alkali metal chloride, alkali earth metal chloride, transition metal chloride and magnesium chloride, sugar and/or sugar alcohol, and alkali metal salt, alkali earth metal salt, transition metal chloride or magnesium salt or its hydrate, and sodium gluconate, those stabilize the compound represented by formula (I), its pharmaceutically acceptable salt or solvate thereof and the sodium salt of the compound represented by formula (II) may be used.

Examples of these combinations include a) the compound represented by formula (I), its pharmaceutically acceptable acid additive salt or a solvate thereof, sodium chloride, sucrose, sodium p-toluene sulfonate and sodium gluconate, b) the compound represented by formula (I), its pharmaceutically acceptable acid additive salt or a solvate thereof, sodium chloride, sucrose, sodium sulfate and sodium gluconate, c) the compound represented by formula (I), its pharmaceutically acceptable acid additive salt or a solvate thereof, sodium chloride, sucrose, sodium p-toluene sulfonate, sodium sulfate and sodium gluconate, d) sodium salt of the compound represented by formula (II), sodium chloride, sucrose, sodium p-toluene sulfonate and sodium gluconate, e) sodium salt of the compound represented by formula (II), sodium chloride, sucrose and sodium sulfate and sodium gluconate, f) sodium salt of the compound represented by formula (II), sodium chloride, sucrose, sodium p-toluene sulfonate, sodium sulfate and sodium gluconate, g) the compound represented by formula (I), its pharmaceutically acceptable acid additive salt or a solvate thereof, magnesium chloride, sucrose, sodium p-toluene sulfonate and sodium gluconate, h) the compound represented by formula (I), its pharmaceutically acceptable acid additive salt or a solvate thereof, magnesium chloride, sucrose, sodium sulfate and sodium gluconate, i) the compound represented by formula (I), its pharmaceutically acceptable acid additive salt or a solvate thereof, magnesium chloride, sucrose, sodium p-toluene sulfonate, sodium sulfate and sodium gluconate, j) sodium salt of the compound represented by formula (II), magnesium chloride, sucrose, sodium p-toluene sulfonate and sodium gluconate, k) sodium salt of the compound represented by formula (II), magnesium chloride, sucrose, sodium sulfate and sodium gluconate, l) sodium salt of the compound represented by formula (II), magnesium chloride, sucrose, sodium p-toluene sulfonate, sodium sulfate and sodium gluconate. Preferably, c), f), and more preferably, f).

When the pharmaceutical preparation comprises sodium chloride as alkali metal chloride, sucrose as sugar and/or sugar alcohol, sodium p-toluene sulfonate as alkali metal salt of p-toluene sulfonate and sodium sulfate as alkali metal salt of sulfuric acid to the compound represented by formula (I), its pharmaceutically acceptable salt or solvate thereof, a content of sodium chloride is 0.7 to 5.0 molar equivalent, sucrose is 0.3 to 4.0 molar equivalent, sodium p-toluene sulfonate is 0.25 to 2.5 molar equivalent, sodium sulfate is 0.025 to 2.0 molar equivalent and sodium gluconate is 0.05 to 1.0 molar equivalent, preferably, the content of sodium chloride is 1.25 to 4.5 molar equivalent, sucrose is 0.5 to 4.0 molar equivalent, sodium p-toluene sulfonate is 0.5 to 2.25 molar equivalent, sodium sulfate is 0.075 to 1.5 molar equivalent and sodium gluconate is 0.075 to 0.75 molar equivalent, more preferably, a content of sodium chloride is 1.5 to 4.0 molar equivalent, sucrose is 1.0 to 3.0 molar equivalent, sodium p-toluene sulfonate is 0.75 to 2.0 molar equivalent, sodium sulfate is 0.1 to 1.0 molar equivalent and sodium gluconate is 0.1 to 0.5 molar equivalent.

When the pharmaceutical preparation comprises sodium chloride as alkali metal chloride, sucrose as sugar and/or sugar alcohol, sodium p-toluene sulfonate and sodium sulfate to the sodium salt of the compound represented by formula (II), a content of sodium chloride is 0.7 to 5.0 molar equivalent, sucrose is 0.3 to 4.0 molar equivalent, sodium p-toluene sulfonate is 0.25 to 2.5 molar equivalent, sodium sulfate is 0.025 to 2.0 molar equivalent and sodium gluconate is 0.05 to 1.0 molar equivalent, preferably, the content of sodium chloride is 1.25 to 4.5 molar equivalent, sucrose is 0.5 to 4.0 molar equivalent, sodium p-toluene sulfonate is 0.5 to 2.25 molar equivalent, sodium sulfate is 0.075 to 1.5 molar equivalent and sodium gluconate is 0.075 to 0.75 molar equivalent, more preferably, a content of sodium chloride is 1.5 to 4.0 molar equivalent, sucrose is 1.0 to 3.0 molar equivalent, sodium p-toluene sulfonate is 0.75 to 2.0 molar equivalent, sodium sulfate is 0.1 to 1.0 molar equivalent and sodium gluconate is 0.1 to 0.5 molar equivalent.

The pharmaceutical preparation of the present invention, those the compound represented by formula (I) its pharmaceutically acceptable salt or solvate thereof and the sodium salt of the compound represented by formula (II) and additives is dissolved or suspended in water and dried. The drying method, those stabilize the compound represented by formula (I), its pharmaceutically acceptable salt or solvate thereof and the sodium salt of the compound represented by formula (II) may be used. Examples of drying method involve vacuum drying method by evaporator, spray-drying method and lyophilized method and the like, preferably lyophilized method, the desirable preparation of the present invention is lyophilized product.

The pharmaceutical preparation of the present invention comprising the compound represented by formula (I), its pharmaceutically acceptable salt or solvate thereof and the sodium salt of the compound represented by formula (II) can be administered as the injection.

A manufacturing process on the pharmaceutical preparation of the present invention comprising at least the following steps:

a) a step of adjusting the liquid comprising the compound represented by formula (I), its pharmaceutically acceptable salt or a solvate thereof:

[Chemical formula 13]

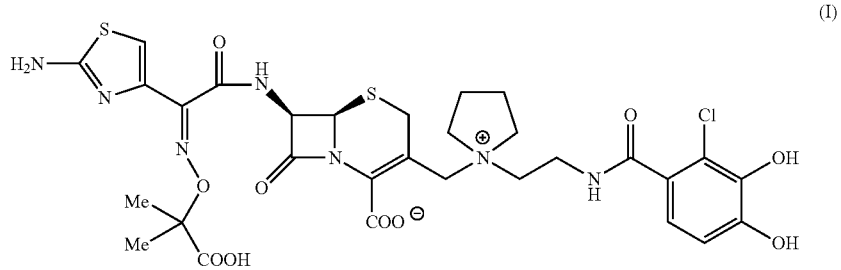

(I)

to pH 5 to 6 by alkali materials,
b) a step of mixing the liquid which is prepared by said step a), said component 2) and said component 3), and
c) a step of lyophilizing the mixture prepared by said step b). The pharmaceutical composition prepared by the above steps can be used as the pharmaceutical preparation of the present invention.

Preferably, the manufacturing process on the pharmaceutical preparation of the present invention comprises at least the following steps:
a) the step of adjusting the liquid comprising the compound represented by formula (I), its pharmaceutically acceptable salt or a solvate thereof to pH 5.5 to 6 by alkali material,
b) the step of mixing the liquid which is prepared by said step a), said component 2) and said component 3), and
c) the step of lyophilizing the mixture manufactured by said step b) (the components 2) and 3) are the same meanings in claim 1.). The pharmaceutical composition prepared by the above steps can be used as the pharmaceutical preparation of the present invention.

More preferably, the manufacturing process of the pharmaceutical preparation comprising at least the following steps:
a) the step of adjusting the suspension comprising the compound represented by formula (I), its pharmaceutically acceptable acidic additive salt or a solvate thereof to pH 5 to 6 by sodium hydroxide.
b) the step of mixing the liquid which is prepared by said step a), said component 2) and said component 3), and
c) the step of lyophilizing the mixture prepared by said step b) (the components 2) and 3) are the same meanings in claim 1.). The pharmaceutical composition prepared by the above steps can be used as the pharmaceutical preparation of the present invention.

More preferably, the manufacturing process of preparation involving the following step at least:
a) the step of adjusting the suspension comprising the compound represented by formula (I), its pharmaceutically acceptable acidic additive salt or a solvate thereof to pH 5.5 to 6 by sodium hydroxide,
b) the step of mixing the liquid which is prepared by said step a), said component 2) and said component 3), and
c) the step of lyophilizing the mixture prepared by said step b) (the components 2) and 3) are the same meanings in claim 1.). The pharmaceutical composition prepared by the above steps can be used as the pharmaceutical preparation of the present invention.

More preferably, the manufacturing process on the pharmaceutical preparation of the present invention comprises at least the following steps:
a) the step of adjusting the suspension comprising p-toluene sulfonate salt and sulfuric acid salt of the compound represented by formula (I) to pH 5.5 to 6 by sodium hydroxide.
b) the step of mixing the liquid which is prepared by said step a), said component 2) and said component 3), and
c) the step of lyophilizing the mixture prepared by said step b) (the components 2) and 3) are the same meanings in claim 1.). The pharmaceutical composition prepared by the above steps can be used as the pharmaceutical preparation of the present invention.

Examples of the manufacturing process on the pharmaceutical preparation of the present invention involve 1) acidic slurry is prepared by adding the compound represented by formula (I), its pharmaceutically acceptable acidic additive salt or a solvate thereof, preferably, the p-toluene sulfonate salt, sulfuric acid salt of the compound represented by formula (I) in the injectable water, 2) sodium chloride is added in the slurry solution of said 1), and pH of the solution is adjusted to pH 5.5 to 6, and the additive is added to stabilize the slurry solution of said 1), 3) injectable water is added additionally and concentration is adjusted to 5 w/w % and the solution is aseptically filtered and formulation solution is completed, 4) the given amount of said 3) formulation solution is dispensed in the vial or ample and the like and formulation is manufactured by lyophilization. The manufacture of the present preparation is preferable under the sealing condition.

As freezing dryer, vacuum freezing fryer can be used.

As the condition of the lyophilization, as the condition of freeze, −50 to −3° C. and 0.5 to 5 hours, preferably, −40 to −5° C. and 1 to 4 hours, as the condition of primary drying, −50 to −10° C. and 0.1 to 150 hours, vacuum pressure is 5 to 20 Pa, preferably, −40 to −20° C. and 0.5 to 130 hours, vacuum pressure is 7.5 to 15 Pa, as the condition of second drying, 15 to 70° C. and 1 to 7 hours, vacuum pressure is 5 to 20 Pa, preferably, 20 to 65° C. and 1.5 to 6.5 hours, vacuum pressure is 5 to 20 Pa.

The lyophilized preparation of the present invention is administered after adding the dissolved solution such as injectable distilled water, physiological saline or glucose solution and dissolving the preparation, timely. The pharmaceutical preparation of the present invention after lyophilizing is administered after adding a solution such as a distilled water for injection, normal saline solution or glucose solution at the time of use to dissolve. The pharmaceutical composition of the present invention exhibits a strong antibacterial spectrum against Gram-positive bacteria and Gram-negative bacteria, especially β-lactamase producing Gram-negative bacteria, and it does not exhibit cross-resistance with existing cephem drugs and carbapenems.

The analog is sometimes produced in the composition comprising the compound represented by the above formula (I). When the composition is stored temporally, the amount of the analog increases more. As the analog, mainly,

[Chemical formula 14]

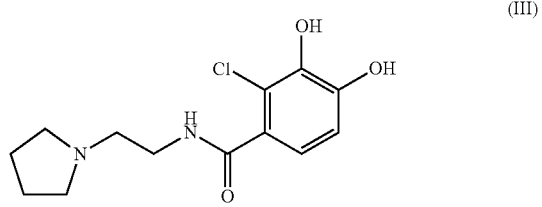 [SMILES: O=C(NCCN1CCCC1)c1ccc(O)c(O)c1Cl]

(III)

the compound represented by formula (III) arises. It is preferable that the increased amount of the compound represented by formula (III) is low under the consideration of toxicity. When the composition of the present invention is preserved at 40° C. for two weeks, the increased amount from the start of test of the compound represented by formula (III) in said medicinal composition is less than 0.45%, preferably, less than 0.425%, more preferably, less than 0.4%. Moreover, when the composition of the present invention was preserved at 25° C. for two weeks, the increased amount from the start of test of the compound represented by formula (III) in said medicinal composition is less than 0.06%, preferably less than 0.055%, more preferably, less than 0.05%, especially preferably, less than 0.04%.

The dimer of the compound represented by formula (I) is produced in the composition comprising the compound represented by formula (I), and when the composition is preserved temporally, the amount of said dimer increases. As the dimer, mainly, the compound represented by formula (IV):

arises. It is preferable that the increased amount of compound represented by formula (IV) is low under the consideration of toxicity. When the composition of the present invention was preserved at 25° C. for two weeks, the increased amount from the start of test of the compound represented by formula (IV) in said medicinal composition is less than 0.06%, preferably, less than 0.055%, more preferably, less than 0.05%, especially preferably, less than 0.04%.

EXAMPLES

The present invention will be explained in more detail below by way of Examples, and Comparative Examples, but these do not limit the present invention.

1. The manufacturing method of the compound represented by formula (I), its pharmaceutically acceptable salt or solvate thereof (1.3 tosilate salt/0.4 sulfuric acid salt)

<Preparation of a Seed Crystal A of 2 Mole Equivalents of p-toluenesulfonic Acid Salt of the Compound (IA)>

The compound (I) (100 mg) was dissolved in 1.0 mol/L p-toluenesulfonic acid solution (2 mL) at room temperature using an ultrasonic, and the resulting solution was left to stand at 4° C., for 4 days. The precipitate was filtered to yield a seed crystal A (73 mg). It was confirmed to be a needle-like crystal by microscope.

<Preparation of the Type I Crystal: A Crystalline Solid of Hydrate of a Mixed Acid Salt of the Compound (IA), Wherein the Mixed Acid Salt was Formed from 1.3 Mole Equivalents of p-Toluene Sulfonate and 0.35 Mole Equivalents of Sulfuric Acid (Synthesis of the Type I)>

Step 1: Preparation of a Seed Crystal C

The seed crystal A (50 mg) was dissolved in 6 mol/L $H_2SO_4$ (3 mL) on an ultrasonic water bath at room temperature, and the solution was left to stand at 4° C. for 2 days. The precipitated crystalline solid was filtered and washed with ice chilled water to yield a seed crystal C (23 mg).

[Chemical formula 15]

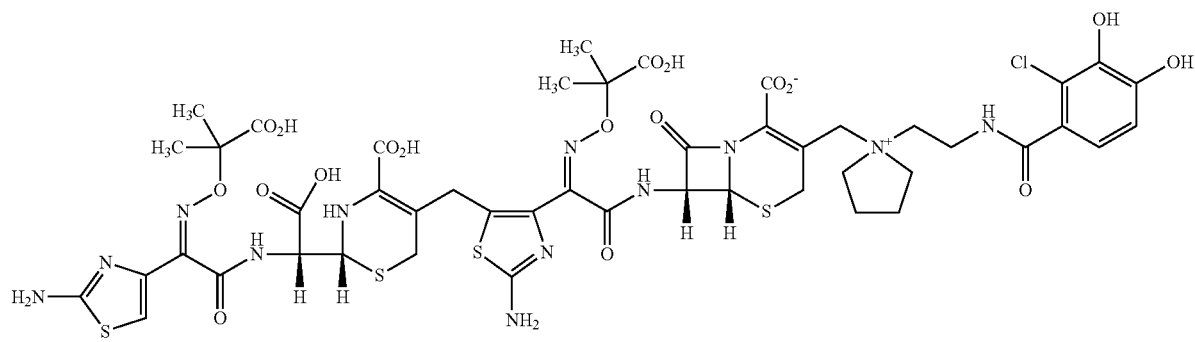

(IV)

Step 2: Synthesis of the Compound 5

[Chemical formula 16]

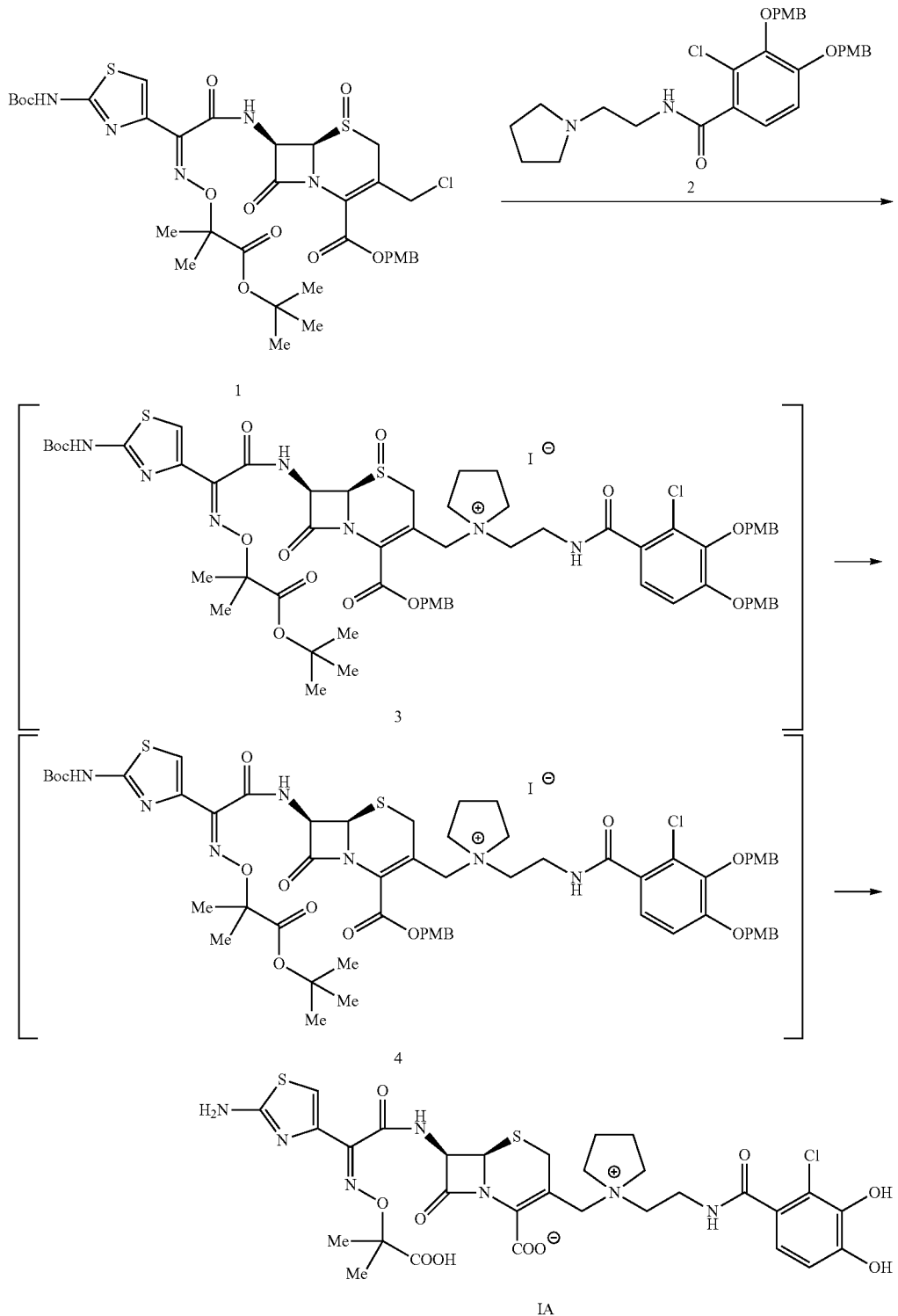

Under a nitrogen atmosphere, the compound 1 (18.0 kg, 22.6 mol) was dissolved in N,N-dimethylacetoamide (41 L), and cooled to 0° C. Sodium iodide (6.8 kg, 45.2 mol), the compound 2 (13.1 kg, 24.9 mol), and N,N-dimethylaceto- amide (4 L) are added to the solution at 0° C. for 6 days. The solution was warmed to 7° C. and stirred for 16 hours. The solution was cooled to 0° C. and sodium iodide (5.1 kg, 33.9 mol) was added to the solution, and then acetyl chloride (8.9 kg, 113.0 mol) was dropped, over 90 minutes at 0° C., the solution was stirred at 0° C. for 5 hours.

Anisole (36 L) was added to the reaction solution, this solution was added to the mixed solution of methyl ethyl ketone and aqueous solution of sodium bisulfite, and extracted. The organic layer was washed with the mixed solution of sulfuric acid and brine twice. Anisole (90 L) was added and the solution was cooled to 15° C. 75% sulfuric acid (36.0 kg) was added to the solution, it was stirred at 28° C. for 2 hours. After adding water (90 L) and ethyl acetate (36 L), the resulting solution was extracted. The obtained aqueous layer was washed with ethyl acetate twice, and then purified by reverse phase column chromatography (acetonitrile-sulfuric acid aqueous solution) using a chromatographic separation small particle size synthetic adsorbent (Diaion™ HP20SS). After adding an aqueous solution of 75% sulfuric acid (33.4 kg) and p-toluenesulfonic acid monohydrate (16.7 kg), it was added an appropriate amount of the seed crystal C to precipitate a solid. It was cooled to 5° C. and stirred at 5° C. for 10 hours, and the precipitated crystalline solid was filtered. The crystalline solid was washed with water cooled to 5° C., and then dried under reduced pressure at about 33 hPa for about 3 hours to yield a type I crystal D of the compound (IA) (12.7 kg, content conversion yield: 49%).

The contents of p-toluenesulfonic acid and sulfuric acid in the type I crystal D were determined by the following method.

(p-Toluenesulfonic Acid Content Measuring Method)

Step 1: Preparation of a Sample Solution

About 40 mg of the sample was weighed precisely, and dissolved in a sample dilution solvent to be exactly 25 mL. To 2 mL of this solution weighed precisely was added a sample dilution solvent to be prepared exactly 20 mL solution.

Step 2: Preparation of a Standard Solution

About 25 mg of a standard preparation of sodium p-toluenesulfonate equilibrated humidity under the condition of 25° C./60% RH was weighed precisely, and dissolved in a sample dilution solvent to be exactly 100 mL. To 5 mL of this solution weighed precisely was added a sample dilution solvent to be prepared exactly 50 mL solution.

5 mmol/L phosphate buffer/liquid chromatography acetonitrile mixture (9:1) was used as the above sample dilution solvent. Herein, water: 0.05 mol/L sodium dihydrogen phosphate test solution: 0.05 mol/L disodium hydrogen phosphate reagent mixture=18:1:1 (pH is about 7.1) was used as a phosphate buffer.

Step 3: Measurement and Determination

The peak area of p-toluenesulfonic acid was determined in an automatic integration method by measuring the above sample solution and the standard solution in the following test condition by liquid chromatography.

(Test Condition)

Column: Unison UK-C18, φ4.6×150 mm, 3 μm, by Imtakt

Column temperature: constant temperature at near 35° C.

Flow rate: 1.0 mL per minute (a retention time of p-toluenesulfonic acid: about 7 minutes)

Detector: ultraviolet absolution spectrophotometer (wavelength: 218 nm)

Mobile phase A: 0.1% trifluoroacetic acid solution

Mobile phase B: acetonitrile for liquid chromatography

TABLE 1

Gradient program

| Time after addition (minute) | Mobile phase A (vol %) | Mobile phase B (vol %) |
|---|---|---|
| 0~7 | 95 | 5 |
| 7~7.01 | 95→60 | 5→40 |
| 7.01~15 | 60 | 40 |
| 15~15.01 | 60→95 | 40→5 |
| 15.01~25 | 95 | 5 |

The content of p-toluenesulfonic acid in the sample was determined using the following formula.

The amount of $p$-toluenesulfonic acid (%) =

$$\frac{M_S}{M_T} \times \frac{P}{100} \times \frac{100}{100-W_T} \times \frac{A_T}{A_S} \times \frac{172.20}{194.18} \times \frac{1}{4} \times 100$$

$M_S$: weighed amount of a standard preparation of sodium p-toluenesulfonate (mg)

$M_T$: weighed amount of a sample (mg)

P: purity of a standard preparation of sodium p-toluene sulfonate (%)

$W_T$: water of a sample (%)

$A_T$: peak area of p-toluene sulfonate obtained from the sample solution $A_S$: peak area of p-toluene sulfonate obtained from the standard solution 172.20: molecular weight of p-toluene sulfonate 194.18: molecular weight of sodium p-toluene sulfonate ¼: dilution rate (Sulfuric Acid Content Measuring Method)

Step 1: Preparation of a Standard Solution

About 50 mg of sodium sulfate anhydrous was weighed precisely, and dissolved in a mobile phase to be exactly 25 mL. To 2 mL of this liquid weighed precisely was added a mobile phase to be exactly 50 mL. Furthermore, to 2 mL of this liquid weighed precisely was added a mobile phase to be exactly 20 mL.

Step 2: Preparation of a Sample Solution

About 30 mg of a sample was weighed precisely, and dissolved in a mobile phase to be exactly 25 mL. To 2 mL of this liquid weighed precisely was added a mobile phase to be exactly 20 mL.

Step 3: Measurement and Determination

The peak area of sulfate ion was determined in an automatic integration method by measuring the above sample solution and the standard solution in the following test condition by liquid chromatography.

(Test Condition)

Column: Shim-pack IC-A3, φ4.6×150 mm, 5 μm, Shimadzu Corporation

Column temperature: constant temperature at near 40° C.

Flow rate: 1.2 mL per minute (a retention time of sulfate ion: about 15 minutes)

Detector: electric conductivity detector (non-suppressor system)

Mobile phase: the solution obtained by the following: about 0.67 g of Bis-Tris, about 3.09 g of boric acid, and about 1.11 g of the ground p-hydroxybenzoic acid weighed precisely were dissolved in water to be exactly 1000 mL.

The content of sulfuric acid in the sample was determined using the following formula.

The amount of sulfuric acid (%)=$M_S/M_T \times 100/(100-W_T) \times A_T/A_S \times 98.08/142.04 \times 1/25 \times 100$ $M_S$: weighed amount of sodium sulfate anhydrous (mg)
$M_T$: weighed amount of a sample (mg)
$W_T$: water of a sample (%)
$A_S$: peak area of sulfate ion obtained from the standard solution
$A_T$: peak area of sulfate ion obtained from the sample solution
98.08: molecular weight of sulfuric acid
142.04: molecular weight of sodium sulfate anhydrous
1/25: dilution rate
(Result)
p-Toluenesulfonic acid: 22.2±0.2% (on an anhydrous basis)
Sulfuric acid: 4.3±0.1% (on an anhydrous basis)
Elemental analysis: (calculated as $C_{30}H_{34}N_7ClO_{10}S_2$, $1.32C_7H_8O_3S$, $0.45H_2SO_4$, $9.0H_2O$)
Calculated: C, 39.75(%), H, 5.39(%), N, 8.27(%), Cl, 2.99(%), S, 10.19(%), $H_2O$, 13.67(%)
Measured: C, 39.73(%), H, 5.33(%), N, 8.53(%), Cl, 3.08(%), S, 10.11(%), $H_2O$, (KF method) 13.69(%)

As described above, the obtained crystalline is I type crystalline which is hydrated crystalline of the mixed acid salt of 1.3 mole equivalent of p-toluene sulfonate and 0.35 mole equivalent of sulfuric acid, which remains about 0.02 mole equivalent of p-toluene sulfonate and about 0.1 mole equivalent of sulfuric acid. That is, type I crystals can be substantially interpreted as the same crystalline solid even if p-toluene sulfonate and/or sulfuric acid may be in the form incorporated into a crystal. The type I crystal may comprise remaining about 0.01 to 0.1 mole equivalents of p-toluene sulfonate and/or about 0.01 to 0.1 mole equivalents of sulfuric acid. The remaining acid may be in the form adhered to a crystal or the form incorporated into a crystal.

The preferable content of p-toluene sulfonate of the type I crystal is about 20.2±0.2 to 23.2±0.2% (on an anhydrous basis), the preferable content of sulfuric acid is about 3.5±0.1 to 5.0±0.1% (on an anhydrous basis). The more preferable content of p-toluenesulfonic acid is about 21.5±0.2 to 22.3±0.2% (on an anhydrous basis), the more preferable content of sulfuric acid is about 4.2±0.1 to 4.9±0.1% (on an anhydrous basis). The further preferable content of p-toluene sulfonate of the type I crystal is about 21.5 to 22.3% (on an anhydrous basis), further preferable content of sulfuric acid is about 4.2 to 4.9% (on an anhydrous basis).

2. Manufacturing Method of Sodium Salt, p-Toluene Sulfonate, Sodium Sulfate

The sodium salt of the compound represented by formula (II) (hereinafter sometimes abbreviated as "sodium salt of formula (II)"), sodium p-toluene sulfonate (hereinafter sometimes abbreviated as "sodium tosylate"), sodium sulfate (hereinafter sometimes abbreviated as "sodium sulfate") is manufactured by the following method. That is, the compound the compound or its pharmaceutically acceptable salt or solvate of a compound represented by formula (I), preferably 500 mg I type crystal converted by the compound represented by formula (I) was weighed and the crystal was suspended in about 6 mL injectable distilled water. The solution was adjusted to pH 5.5 to 6 by 2N sodium hydroxide and the compound represented by formula (I) was dissolved as sodium salt of the compound represented by formula (II). The additives to stabilize are added, and the injectable water is added additionally and concentration is adjusted to 5 w/w % and the solution is aseptically filtered and formulation solution is prepared. The given amount of said formulation solution is filled into the vial or ample and the like, and formulation is manufactured by lyophilization. By this method, the solution comprising the sodium salt of compound represented by formula (II) converted by 500 mg compound represented by formula (I). 129.1 mg sodium p-toluene sulfonate, and 47.2 mg sodium sulfate was manufactured. The active ingredient of following example exists to sodium salt of the compound represented by formula (I), in the table, converted by the compound represented by formula (I).

3. Examination of Comprising Amount of Alkali Metal Chloride in the Pharmaceutical Preparation of the Present Invention After formulation of Table 2 was manufactured, the pharmaceutical preparation was stored at 40° C. for two weeks, and the increased amount of analog (formula (III) compound) was measured to examine the content of sodium chloride which is alkali metal chloride.

The pharmaceutical preparation of table 2 was manufactured as follows. 500 mg I type crystalline was weighed, which is converted by the compound represented by formula (I), and this crystal was suspended in the injectable distilled water of the about 6 mL. The suspended solution was adjusted to pH 5.5 to 6 by 2N sodium hydroxide, and the solution was dissolved as the sodium salt of compound represented by formula (II). The sodium salt of compound represented by this formula (II), which is converted by 500 mg of the compound represented by formula (II), was mixed with desired amount of sucrose (Wako), sodium chloride (Merck) and sodium gluconate (ROQUETTE, hereafter, it may be abbreviated as "gluconate Na") and dissolved in the solution comprising 129.1 mg of p-toluene sulfonate and 47.2 mg of sulfuric acid. The solution was filtered aseptically by the membrane of PVDF having 0.2 μm pore size. The obtained filtrate was filled into the glass container and it was lyophilized (Example 1, Reference example 1, Comparative example 1 to 3).

As the condition of lyophilization, 1) cooling at 5° C., 2) cooling at −5° C. for 1 hour, 3) freezing at −40° C. for 4 hours, 4) primary drying at −22° C. for 129 hours under 10 Pa degree of vacuum, 5) second drying at 60° C. for 6 hours under 10 Pa degree of vacuum was conducted and the lyophilized product was manufactured (Example 1, 2, Comparative example 1 to 4).

TABLE 2

|  | Comparative Example 1 | Comparative Example 2 | Comparative Example 3 | Example 1 | Example 2 | Comparative Example 4 |
|---|---|---|---|---|---|---|
|  |  |  |  |  |  | (Unit: mg) |
| Sodium salt represented by formula (II) | 500.0 | 500.0 | 500.0 | 500.0 | 500.0 | 500.0 |

TABLE 2-continued

|  | Comparative Example 1 | Comparative Example 2 | Comparative Example 3 | Example 1 | Example 2 | (Unit: mg) Comparative Example 4 |
|---|---|---|---|---|---|---|
| p-toluene sulfonate | 129.1 | 129.1 | 129.1 | 129.1 | 129.1 | 129.1 |
| Sodium sulfuric acid | 47.2 | 47.2 | 47.2 | 47.2 | 47.2 | 47.2 |
| Sucrose | 450.0 | 450.0 | 450.0 | 450.0 | 450.0 | 450.0 |
| Sodium chloride | — | 25.0 | 50.0 | 108.0 | 150.0 | 200.0 |
| Sodium gluconate | 28.6 | 28.6 | 28.6 | 28.6 | 28.6 | 28.6 |

*: Conversion of the compound represented by formula (I)

(The Measuring Method of Compound Represented by Formula (III), which is an Analog)

(1) Preparation of a Sample Solution

About 8 mL of solvent to dilute the sample was added into 1 vial of the present preparation and dissolved, and it was transferred into 50 mL measuring flask by pipette. This operation was repeated for four times, and the content in the vial was washed thoroughly and add the sample solution solvent to be prepared exactly 50 mL solution. To 2 mL of this solution weighed precisely was added a sample dilution solvent to be prepared exactly 20 mL solution.

(2) Measuring Method

The peak area of the compound represented by formula (I) was determined in an automatic integration method by measuring in the following test condition by liquid chromatography.

(Test condition of liquid chromatography)

Detector: ultraviolet absorption spectrophotometer (Measuring wave length: 261 nm)

Sampling rate: 20 points/sec.

Column: YMC-lUtraHT Pro C18, ⌀2.0×100 mm, 2 Mm, YMC

Column temperature: constant temperature at near 35° C.

Mobile phase A: trifluoroacetic acid test solution

Mobile phase B: acetonitrile for liquid chromatography

TABLE 3

Gradient program

| Time after addition (min) | Mobile phase A (vol %) | Mobile phase B (vol %) | Gradient curve |
|---|---|---|---|
| 0-0.6 | 95 -> 90 | 5 -> 10 | 6 |
| 0.6-3.3 | 90 -> 88 | 10 -> 12 | 6 |
| 3.3-4.5 | 88 | 12 | 6 |
| 4.5-7.0 | 88 -> 87 | 12 -> 13 | 6 |
| 7.0-12.4 | 87 -> 65 | 13 -> 35 | 7 |
| 12.4-12.5 | 65 -> 95 | 35 -> 5 | 6 |
| 12.5-15.0 | 95 | 5 | 6 |

Flow rate: 0.5 mL per minute (a retention time of the compound represented by formula (I): about 5 minutes)

Injectable volume: 2 μL

Sample roop: 10 μL, partial roop (needle over fil)

Week solvent: water 600 μL

Strong solvent: water 200 μL

Sample cooler temperature: constant temperature of about 5° C.

Washing solution of Auto injector: water (4) Calculation Equation $$\text{The amount of compound represented by formula (III) (\%)} = \frac{A_i}{A_T} \times 100$$

$A_i$: peak area of the compound represented by formula (III) except for p-toluene sulfonate $A_T$: sum of peak area except for the system peak and p-toluene sulfonate By the above calculation equation, the amount (%) of compound represented by equation (III) in the pharmaceutical preparation was calculated at the start of test and after the storage at 40° C. for two weeks, respectively. The amount of compound represented by formula (III) at the time of test start was subtracted from the amount of compound represented by formula (III) after the storage at 40° C. for two weeks. This subtraction was "the increased amount of the compound represented by formula (III)".

(The Measuring Method of Glass Transition Temperature)

The glass transition temperature was measured by the general test described in 15th revised Japanese Pharmacopoeia, the method of differential scanning calorimetry (DSC) which is the first method of thermal analysis.

The increased amount of the compound represented by formula (III), which is the analog is shown in table 4. As a result, the increased amount of the compound represented by formula (III) of Example 1 and 2 was the lowest and the pharmaceutical preparation of Example 1 and 2 was stable. Further, in the pharmaceutical preparation of Example 1, the content of sodium chloride is 2.8 mole equivalent, the content of sucrose is 2.0 mole equivalent, the content of sodium p-toluene sulfonate is 1.0 mole equivalent, the content of sodium sulfonic acid is 0.5 mole equivalent, the content of sodium gluconate is 0.2 mole equivalent to the compound represented by formula (I). Moreover, in the pharmaceutical preparation of Example 2, the content of sodium chloride is 3.9 mole equivalent, the content of sucrose is 2.0 mole equivalent, the content of sodium p-toluene sulfonate is 1.0 mole equivalent, the content of sodium sulfonic acid is 0.5 mole equivalent, the content of sodium gluconate is 0.2 mole equivalent to the compound represented by formula (I). In comparative example 4, the increased amount of the compound represented by formula (III) was low, but the glass transition temperature was lower than −40° C., and it was thought that the stable glass state could not be preserved.

TABLE 4

|  | Comparative Example 1 | Comparative Example 2 | Comparative Example 3 | Example 1 | Example 2 | Comparative Example 4 |
|---|---|---|---|---|---|---|
| The increased amount of the compound represented by formula (III) (%) | 0.7 | 0.6 | 0.5 | 0.3 | 0.3 | 0.3 |
| Glass transition temperature (° C.) | −26 | −27 | −32 | −37 | −40 | −43 |

5. The Examination on the Type of Sugar or Sugar Alcohol in the Pharmaceutical Preparation of Present Invention To examine the type of sugar or sugar alcohol, the increased amount of the compound which is the analog after manufacturing of pharmaceutical preparation of Table 5, which is stored at 4° C. for two weeks (Example 1, Comparative example 5, 6). The manufacturing method of pharmaceutical preparation and the measuring method of the analog is same as Example 1.

TABLE 5

| | Example 1 | Comparative Example 5 | (Unit: mg) Comparative Example 6 |
|---|---|---|---|
| Sodium salt of the compound represented by formula (II) | 500.0 | 500.0 | 500.0 |
| Sodium p-toluene sulfonate | 129.1 | 129.1 | 129.1 |
| Sodium sulfate | 47.2 | 47.2 | 47.2 |
| Sucrose | 450.0 | — | 450.0 |
| Trehalose | — | 450.0 | — |
| D-mannitol | — | — | 450.0 |
| Sodium chloride | 108.0 | 108.0 | 108.0 |
| Sodium gluconate | 28.6 | 28.6 | 28.6 |

*: Conversion of the compound represented by formula (I)

The measuring result of increased amount of the compound represented by formula (III), which is the analog, is shown in Table 6. As a result, the increased amount of analogue in Example 1 comprising sucrose was the lowest and the pharmaceutical preparation of Example 1 was stable.

TABLE 6

| | Example 1 | Comparative Example 5 | Comparative Example 6 |
|---|---|---|---|
| Increased amount of the compound represented by formula (III) (%) | 0.3 | 0.4 | 2.3 |

6. The Examination on the Amount of Sucrose in the Pharmaceutical Preparation of Present Invention To examine the amount of sucrose, the increased amount of the compound which is the analog after manufacturing of pharmaceutical preparation of Table 7, which is stored at 40° C. for two weeks (Example 1, 3, 4, Comparative example 7, 8). The manufacturing method of pharmaceutical preparation and the measuring method of the analog are same as Example 1.

TABLE 7

| | Comparative Example 3 | Comparative Example 8 | Example 3 | Example 1 | (Unit: mg) Example 4 |
|---|---|---|---|---|---|
| Sodium salt represented by formula (II) | 500.0* | 500.0* | 500.0* | 500.0* | 500.0* |
| Sodium p-toluene sulfonate | 129.1 | 129.1 | 129.1 | 129.1 | 129.1 |
| Sodium sulfuric acid | 47.2 | 47.2 | 47.2 | 47.2 | 47.2 |
| Sucrose | 112.5 | 225.0 | 337.5 | 450.0 | 562.5 |
| Sodium chloride | 108.0 | 108.0 | 108.0 | 108.0 | 108.0 |
| Sodium gluconate | 28.6 | 28.6 | 28.6 | 28.6 | 28.6 |

*Conversion of the compound represented by formula (I)

The measuring result on the increased amount of the compound represented by formula (III), which is the analog, is shown in table 8. As a result, the increased amount of the analog of Example 1, 3 and 4 was the lowest and the pharmaceutical preparation of Example 1, 3 and 4 was stable. Further, in the pharmaceutical preparation of Example 3, the content of sodium chloride is 2.8 mole equivalent, the content of sucrose is 1.5 mole equivalent, the content of sodium p-toluene sulfonate is 1.0 mole equivalent, the content of sodium sulfonic acid is 0.5 mole equivalent, the content of sodium gluconate is 0.2 mole equivalent to the compound represented by formula (I). Moreover, in the pharmaceutical preparation of Example 4, the content of sodium chloride is 2.8 mole equivalent, the content of sucrose is 2.5 mole equivalent, the content of sodium p-toluene sulfonate is 1.0 mole equivalent, the content of sodium sulfonic acid is 0.5 mole equivalent, the content of sodium gluconate is 0.2 mole equivalent to the compound represented by formula (I).

TABLE 8

| | Comparative Example 7 | Comparative Example 8 | Example 1 | Example 2 | Example 4 |
|---|---|---|---|---|---|
| The increased amount of the compound represented by formula (III) (%) | 0.7 | 0.4 | 0.3 | 0.3 | 0.3 |

7. Effect of Sucrose and Sodium Chloride in the Pharmaceutical Preparation of the Present Invention To examine the effect of sucrose and sodium chloride, the residual ratio of the compound represented by formula (I) after manufacturing of preparation of Table 9, which is stored at 40° C. for two weeks was measured (Example 5, 6). The manufacturing method of pharmaceutical preparation is same as Example 1.

TABLE 9

|  | Example 5 | Example 6 |
|---|---|---|
|  |  | (Unit: mg) |
| Sodium salt represented by formula (II) | 500.0* | 500.0* |
| Sodium p-toluene sulfonate | 129.1 | 129.1 |
| Sodium sulfuric acid | 47.2 | 47.2 |
| Sucrose | 450.0 | — |
| Sodium chloride | 108.0 | — |

*Conversion of the compound represented by formula (I)

(Measuring Method on the Residual Rate of the Compound Represented by Formula (I))

(1) Preparation of a Sample Solution

About 8 mL of solvent to dilute the sample was added into 1 vial of the present preparation and dissolved, and it was transferred into 50 mL measuring flask by pipette. This operation was repeated for four times, and the content in the vial was washed thoroughly and add the sample solution solvent to be prepared exactly 50 mL solution. To 2 mL of this solution weighed precisely was added a sample dilution solvent to be prepared exactly 20 mL solution.

(2) Preparation of a Standard Solution

To about 40 mg of reference standard weighed precisely was added a sample dilution solvent to be prepared exactly 25 mL solution, which is the standard solution.

(3) Measuring Method

The peak area of the compound represented by formula (I) was determined in an automatic integration method by measuring in the following test condition by liquid chromatography.

(Test condition of liquid chromatography)

Detector: ultraviolet absorption spectrophotometer (Measuring wave length: 261 nm)

Sampling rate: 20 points/sec.

Column: YMC-lUtraHT Pro C18, ¢2.0×100 mm, 2 µm, YMC

Column temperature: constant temperature at near 35° C.

Mobile phase A: trifluoroacetic acid test solution

Mobile phase B: acetonitrile for liquid chromatography

Gradient program

TABLE 10

| Time after addition (min) | Mobile phase A (vol %) | Mobile phase B (vol %) | Gradient curve |
|---|---|---|---|
| 0-0.6 | 95 -> 90 | 5 -> 10 | 6 |
| 0.6-3.3 | 90 -> 88 | 10 -> 12 | 6 |
| 3.3-4.5 | 88 | 12 | 6 |
| 4.5-7.0 | 88 -> 87 | 12 -> 13 | 6 |
| 7.0-12.4 | 87 -> 65 | 13 -> 35 | 7 |
| 12.4-12.5 | 65 -> 95 | 35 -> 5 | 6 |
| 12.5-15.0 | 95 | 5 | 6 |

Flow rate: 0.5 mL per minute (a retention time of the compound represented by formula (I): about 5 minutes)

Injectable volume: 2 µL

Sample roop: 10 µL, partial roop (needle over fil)

Week solvent: water 600 µL

Strong solvent: water 200 µL

Sample cooler temperature: constant temperature of about 5° C.

Washing solution of Auto injector: water (4) Calculation Equation

The content of the compound represented by formula (I) (%) =

$$M_S \times \frac{1}{X} \times \frac{C}{1000} \times \frac{A_T}{A_S} \times 20 \times 100$$

$M_S$: weighed amount of a standard preparation of the compound represented by formula (I) (mg)

X: displayed amount per the present one vial (mg)

C: content of a standard preparation of the compound represented by formula (I) (µg/mg)

$A_S$: peak area of the compound represented by formula (I) obtained from the standard solution $A_T$: peak area of the compound represented by formula (I) obtained from the test solution 20: dilution rate The residual rate of the compound represented by formula (I) is shown in table 11. As a result, the residual rate of the compound represented by formula (I) in Example 5 comprising sucrose and sodium chloride was higher compared with Example 6 which did not comprise sucrose and sodium chloride, and the pharmaceutical preparation of Example 5 was stable. Further, in the pharmaceutical preparation of Example 5, the content of sodium chloride is 2.8 mole equivalent, the content of sucrose is 2.0 mole equivalent, the content of sodium p-toluene sulfonate is 1.0 mole equivalent, the content of sodium sulfonic acid is 0.5 mole equivalent to the compound represented by formula (I). Moreover, in the pharmaceutical preparation of Example 6, the content of sodium p-toluene sulfonate is 1.0 mole equivalent, the content of sodium sulfonic acid is 0.5 mole equivalent to the compound represented by formula (I).

TABLE 11

|  | Example 5 | Example 6 |
|---|---|---|
| Residual rate of the compound represented by formula (I) (%) | 96.1 | 76.8 |

8. Effect of Sodium p-Toluene Sulfonate and Sodium Sulfonic Acid in the Pharmaceutical Preparation of the Present Invention To examine the effect of sodium p-toluene sulfonate and sodium sulfonic add, the residual ratio of the compound represented by formula (I) after manufacturing of pharmaceutical preparation of Table 12, which is stored at 40° C. for two weeks, was measured (Example 6, 7, 8, comparative example 9). The measuring method of residual rate of the compound represented by formula (I) is same as Example 5.

Furthermore, the pharmaceutical preparation of example 6 was manufactured as follows. That is, 500 mg I type crystalline was weighed, which is converted by the compound represented by formula (I), and this crystal was suspended in the injectable distilled water of the about 6 mL. The suspended solution was adjusted to pH 5.5 to 6 by 2N sodium hydroxide, and the solution was dissolved as the sodium salt of compound represented by formula (II). The solution comprising the sodium salt of compound represented by this formula (II) was lyophilized and the pharmaceutical preparation of example 6 was manufactured. In the comparative example 9, the solution comprising the sodium salt of compound represented by said formula (II) was lyophilized. In the example 7, the toluene sulfonate salt was added in the solution comprising sodium salt of compound represented by said formula (II), and the solution was lyophilized. In the example 8, the sulfuric acid salt was added in the solution comprising sodium salt of compound represented by said formula (II), and the solution was lyophilized.

TABLE 12

|  | Comparative Example 9 | Example 6 | Example 7 | Example 8 |
| --- | --- | --- | --- | --- |
| | | | | (Unit: mg) |
| Sodium salt represented by formula (II) | 500.0* | 500.0* | 500.0* | 500.0* |
| Sodium p-toluene sulfonate | — | 129.1 | 129.1 | — |
| Sodium sulfuric acid | — | 47.2 | — | 47.2 |

*Conversion of the compound represented by formula (I)

The residual rate of the compound represented by formula (I) is shown in table 13. As a result, the residual rate of the compound represented by formula (I) in Example 6 to 8 comprising sodium p-toluene sulfonate and sodium sulfate was higher compared with comparative example 9, which did not comprise sodium p-toluene sulfonate and sodium sulfate, and the pharmaceutical preparation of Examples 6 to 8 were stable. Further, in the pharmaceutical preparation of Example 7, the content of sodium p-toluene sulfonate is 1.0 mole equivalent to the compound represented by formula (I). Moreover, in the pharmaceutical preparation of Example 8, the content of sodium sulfate is 0.5 mole equivalent to the compound represented by formula (I).

TABLE 13

|  | Comparative Example 9 | Example 6 | Example 7 | Example 8 |
| --- | --- | --- | --- | --- |
| Residual rate of the compound represented by formula (I) (%) | 57.1 | 76.8 | 74.5 | 61.8 |

9. Optimized Manufacturing Method of Pharmaceutical Preparation

To optimize the manufacturing method of pharmaceutical preparation, 1) the amount of compound per 1 vial increased, 2) the amount of additive decreased, and the pharmaceutical preparation was manufactured. In the pharmaceutical preparation of example 9, the active ingredient and additive of an amount of 2 times of above example 5 is added, and in the pharmaceutical preparation of comparative example 10, the amount of sodium chloride and sucrose in the example 9 decreased. The content of the compound represented by formula (I) immediately after the pharmaceutical preparation of formulation in table 14, and when said formulation was stored at 25° C. for two weeks, an increased amount on the analog, which is represented by formula (III), of the compound represented by formula (I) in the pharmaceutical preparation, and the increased amount on the dimer, which is represented by formula (IV), of the compound represented by formula (I) in the pharmaceutical preparation was measured. Furthermore, as the reference, when the pharmaceutical preparation of example 5 was stored at 25° C. for two weeks, the increased amount of the compound represented by formula (III) and the compound represented by formula (IV) was measured, respectively.

TABLE 14

|  | Example 9 | Comparative Example 10 | Example 5 |
| --- | --- | --- | --- |
| | | | (Unit: mg) |
| Sodium salt represented by formula (II) | 1000.0* | 1000.0* | 500.0* |
| Sodium p-toluene sulfonate | 258.16 | 258.16 | 129.1 |
| Sodium sulfate | 94.46 | 94.46 | 47.2 |
| Sucrose | 900.0 | 150.0 | 450.0 |
| Sodium chloride | 216.0 | 60.0 | 108.0 |

*Conversion of the compound represented by formula (I)

(Manufacturing Method of Pharmaceutical Preparation of Example 9)

1000 mg I type crystalline was weighed, which is converted by the compound represented by formula (I), and this crystal was added into the vial bottle, and it was suspended in the injectable distilled water. The suspended solution was adjusted to pH 5.5 to 6 by 3N sodium hydroxide, and the solution was dissolved as the sodium salt of compound represented by formula (II). 900 mg sucrose (Merck) and 216 mg sodium chloride (Merck) was added into this solution. After the solution was stirred and dissolved, the injectable distilled water was added into the solution and the concentration of the compound represented by formula (I) was adjusted to 10 w/w %. The solution was filtered aseptically and the pharmaceutical preparation solution was prepared. The given amount of obtained solution was filled into the vial or ample and the like and it was lyophilized. As the condition of lyophilization, 1) cooling at 5° C., 2) cooling at −5° C. for 2 hours, 3) freezing at −47.5° C. for 4 hours, 4) freezing at −25° C. for 2 hours, 5) freezing at −40° C. for 1 hour, 5) primary drying at −20° C. for more than 130 hours under 10 Pa degree of vacuum, 6) secondary drying at 60° C. for more than 6 hours under 10 Pa degree of vacuum, was conducted and the lyophilized product was manufactured.

(Manufacturing Method of Pharmaceutical Preparation of Comparative Example 10)

1000 mg I type crystalline was weighed, which is converted by the compound represented by formula (I), and this crystal was added into the vial bottle, and it was suspended in the injectable distilled water. The suspended solution was adjusted to pH 5.5 to 6 by 3N sodium hydroxide, and the solution was dissolved as the sodium salt of compound represented by formula (II). 150 mg sucrose (Merck) and 60 mg sodium chloride (Merck) was added into this solution. After the solution was stirred and dissolved, the injectable distilled water was added into the solution and the concentration of the compound represented by formula (I) was adjusted to 17 w/w %. The solution was filtered aseptically and the pharmaceutical preparation solution was prepared. The given amount of obtained solution was filled into the vial or ample and the like, and it was lyophilized. As the condition of lyophilization, 1) cooling at 5° C., 2) cooling at −5° C. for 1 hour, 3) freezing at −40° C. for 12 hours, 4) freezing at −10° C. for 2 hours, 5) freezing at −40° C. for 2 hours, 5) primary drying at −5° C. for more than 50 hours under 10 Pa degree of vacuum, 6) secondary drying at 60° C. for more than 3 hours under 10 Pa degree of vacuum, was conducted and the lyophilized product was manufactured.

(Measuring Method on Content of the Compound Represented by Formula (I) in the Pharmaceutical Preparation of Example 9 and Comparative 10 Immediately after the Manufacturing of Pharmaceutical Preparation)

(1) Preparation of a Sample Solution

Immediately after manufacturing of the pharmaceutical preparation, about 10 mL of solvent to dilute the sample was added into 1 vial of the present preparation and dissolved, and it was transferred into 100 mL measuring flask by pipette. This operation was repeated for four times, and the content in the vial was washed thoroughly and add the solvent to dilute sample to be prepared exactly 100 mL solution. To 2 mL of this solution weighed precisely was added a solvent to dilute sample to be prepared exactly 20 mL solution, and sample solution was manufactured.

(2) Preparation of a Standard Solution

To about 40 mg of I type crystal weighed precisely was added a solvent to dilute sample to be prepared exactly 25 mL solution. To 2 mL of this solution weighed precisely was added a solvent to dilute sample to be prepared exactly 20 mL solution, and standard solution was manufactured.

(3) Measuring Method

The peak area of the compound represented by formula (I) was determined in an automatic integration method by measuring in the following test condition by liquid chromatography.

(Test condition of liquid chromatography)

Detector: ultraviolet absorption spectrophotometer (Measuring wave length: 261 nm)

Column: Unison UK-C18, ⌀4.6×100 mm, 3 μm, Imtakt

Column temperature: constant temperature at near 35° C.

Mobile phase: trifluoroacetic acid test solution/acetonitrile mixed solution (43:7)

Flow rate: 1.0 mL per minute (a retention time of the compound represented by formula (I): about 6 minutes)

Injectable volume: 10 μL

Sample cooler temperature: constant temperature of about 5° C.

Washing solution of Auto injector: water/acetonitrile mixed solution (1:1)

(4) Calculation Equation

The amount of the compound represented by formula (I) (%) =

$$M_S \times \frac{1}{1000} \times \frac{C}{1000} \times \frac{A_T}{A_S} \times 40 \times 100$$

$M_S$: weighed amount of a standard preparation of toluene sulfonate salt, sulfuric acid salt (1.3 toluene sulfonate salt/ 0.4 sulfuric acid salt) of the compound represented by formula (I) (mg)

1000: displayed amount per the present one vial (mg)

C: content of a standard preparation of toluene sulfonate salt, sulfuric acid salt (1.3 toluene sulfonate salt/0.4 sulfuric acid salt) the compound represented by formula (I) (μg/mg)

$A_S$: peak area of the compound represented by formula (I) obtained from the standard solution $A_T$: peak area of the compound represented by formula (I) obtained from the test solution 40: dilution rate The content of the compound represented by formula (I) in the example 9 and the comparative example 10 immediately after the manufacturing of pharmaceutical preparation is shown in table 15. As a result, the content of the compound represented by formula (I) in formulation of example 9 was about 100%. On the other hand, the content of the compound represented by formula (I) in formulation of comparative example 9, which reduced the amount of sodium chloride and sucrose, was about 97%, the content was not 100%. Further, in the pharmaceutical preparation of Example 9, the content of sodium chloride is 2.8 mole equivalent, the content of sucrose is 2.0 mole equivalent, the content of sodium p-toluene sulfonate is 1.0 mole equivalent, the content of sodium sulfonic acid is 0.5 mole equivalent to the compound represented by formula (I).

TABLE 15

|  | Example 9 (n = 30) | Comparative Example 10 (n = 4) |
| --- | --- | --- |
| Content of the compound represented by formula (I) (%) | 99.2 ± 0.5 | 97.0 ± 0.2 |

(Measuring Method of the Compound Represented by Formula (III) and Formula (IV) in the Pharmaceutical Preparation of Example 9 and Comparative Example 10)

(1) Preparation of a Sample Solution

To about 40 mg of the present preparation weighed precisely was dissolved in a solvent to dilute sample to be prepared exactly 25 mL solution.

(2) Measuring Method

The peak area of the compound represented by formula (III) and formula (IV) was determined in an automatic integration method by measuring in the following test condition by liquid chromatography.

(Test condition of liquid chromatography)

Detector: ultraviolet absorption spectrophotometer (Measuring wave length: 261 nm)

Sampling rate: 20 points/second

Column: COETECS™UPLC C18, ⌀2.1×150 mm, 1.6 μm (Waters)

Column temperature: constant temperature at near 35° C.

Mobile phase A: diluted trifluoroacetic acid (1→500)/ acetonitrile mixed solution for liquid chromatography (97: 3.)

Mobile phase B: acetonitrile for liquid chromatography

TABLE 16

| Gradient program | | |
| --- | --- | --- |
| Time after addition (min) | Mobile phase A (vol %) | Mobile phase B (vol %) |
| 0-0.5 | 95 -> 90 | 5 -> 10 |
| 0.5-4 | 90 -> 88 | 10 -> 12 |
| 4-9 | 88 | 12 |
| 9-30 | 88 -> 87 | 12 -> 13 |
| 30-30.01 | 87 -> 65 | 13 -> 35 |
| 30.01-35 | 65 -> 95 | 35 -> 5 |

Flow rate: 1.0 mL per minute

Sample cooler temperature: constant temperature of about 5° C.

Injectable volume: 2 μL

Range of measured area: for about 30 minutes after injection of sample

Purged solvent: water/acetonitrile mixed solution (9:1)

Washing solution of needle: water/acetonitrile mixed solution (9:1)

(3) Calculation Equation

The amount of compound represented by formula (III) or formula (IV) (%) = $\frac{A_i}{A_T} \times 100$ $A_i$: peak area of the compound represented by formula (III) or formula (IV) except for p-toluene sulfonate $A_r$: sum of peak area except for the system peak and p-toluene sulfonate By the above calculation equation, the amount (%) of compound represented by formula (III) or formula (IV) in the pharmaceutical preparation was calculated respectively at the start of test and after the storage at 25° C. for two weeks, respectively. The amount of compound represented by formula (III) or formula (IV) at the time of test start was subtracted from the amount of compound represented by formula (III) or formula (IV) after the storage at 25° C. for two weeks. This subtraction represented "the increased amount of the compound represented by formula (III)", "the increased amount of the compound represented by formula (IV)".

The increased amount in the pharmaceutical preparation of the compound represented by formula (III) or formula (IV) after the storage of the pharmaceutical preparation of example 9, comparative example 10 and example 5 at 25° C. and for 14 days is shown in table 16. As a result, in the pharmaceutical preparation of example 9, the increased amount of the compound represented by formula (III) or formula (IV) in the pharmaceutical preparation was lower compared with the pharmaceutical preparation of comparative example 10, which reduced the amount of sodium chloride and sucrose, and the increased amount of the compound represented by formula (III) or formula (IV) in the pharmaceutical preparation of example 9 was almost same compared with the pharmaceutical preparation of example 5, which was stable.

TABLE 17

|  | Example 9 | Comparative Example 10 | Example 5 |
|---|---|---|---|
| The increased amount of the compound represented by formula (III) (%) | 0.02 | 0.05 | 0.01 |

TABLE 17-continued

|  | Example 9 | Comparative Example 10 | Example 5 |
|---|---|---|---|
| The increased amount of the compound represented by formula (IV) (%) | 0 | 0.05 | 0 |

AVAILABILITY IN THE INDUSTRY

The pharmaceutical preparation of the present invention is useful as the injection of antibiotics which has strong antibacterial activity and high stability against gram negative bacteria which product β-lactamase.

The invention claimed is:
1. A pharmaceutical composition comprising:
1) a compound of formula (I):

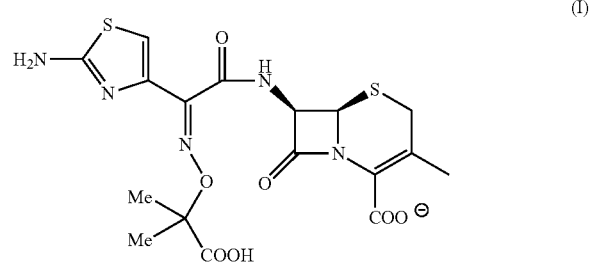

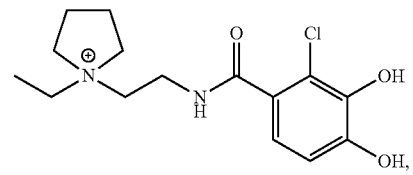

or pharmaceutically acceptable salt or solvate thereof;
2) one or more selected from the group consisting of alkali metal chloride, alkali earth metal chloride, transition metal chloride and magnesium chloride; and
3) a sugar and/or a sugar alcohol.
2. The pharmaceutical composition according to claim 1, wherein said component 1) is a sodium salt represented by formula (II):

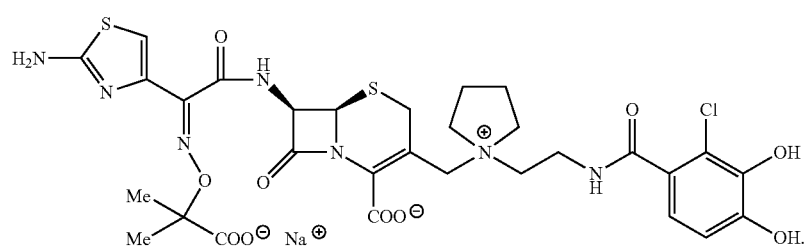

3. The pharmaceutical composition according to claim 1, wherein said component 1) is amorphous.

4. The pharmaceutical composition according to claim 1, which further comprises alkali metal salt, alkali earth metal salt, transition metal chloride or magnesium chloride of an organic acid or inorganic acid, or its hydrate.

5. The pharmaceutical composition according to claim 4, wherein said acid is one or more selected from the group consisting of p-toluenesulfonic acid, benzenesulfonic acid, sulfuric acid, hydrochloric acid and hydrobromic acid.

6. The pharmaceutical composition according to claim 4, wherein said acid is p-toluenesulfonic acid and/or sulfuric acid.

7. The pharmaceutical composition according to claim 4, wherein said salt is sodium salt.

8. The pharmaceutical composition according to claim 7, which comprises alkali metal chloride, wherein said alkali metal chloride is sodium chloride or potassium chloride.

9. The pharmaceutical composition according to claim 8, which comprises alkali metal chloride, wherein said alkali metal chloride is sodium chloride.

10. The pharmaceutical composition according to claim 1, which comprises alkali earth metal chloride, wherein said alkali earth metal chloride is calcium chloride.

11. The pharmaceutical composition according to claim 1, which comprises transition metal chloride, wherein said transition metal chloride is zinc chloride.

12. The pharmaceutical composition according to claim 1, wherein said sugar or sugar alcohol is one or more selected from the group consisting of monosaccharide, disaccharide and polysaccharide.

13. The pharmaceutical composition according to claim 12, wherein sugar or sugar alcohol is one or more selected from the group consisting of glucose, fructose, sucrose, mannitol and trehalose.

14. The pharmaceutical composition according to claim 12, which comprises sugar or sugar alcohol, wherein said sugar or sugar alcohol is sucrose.

15. The pharmaceutical composition according to claim 1, which comprises alkali metal chloride, and sugar or sugar alcohol, wherein said alkali metal chloride is sodium chloride, and said sugar or sugar alcohol is sucrose.

16. The pharmaceutical composition according to claim 15, which comprises sodium chloride of 0.7 to 5.0 mole equivalent as alkali metal chloride, and sucrose of 0.3 to 4.0 mole equivalent as sugar or sugar alcohol, to said component 1).

17. The pharmaceutical composition according to claim 16, which further comprises alkali metal salt of p-toluenesulfonic acid of 0.25 to 2.5 mole equivalent, and alkali metal salt of sulfuric acid of 0.05 to 2.0 mole equivalent, to said component 1).

18. The pharmaceutical composition according to claim 15, which comprises sodium chloride of 0.7 to 5.0 mole equivalent as alkali metal chloride, and sucrose of 0.3 to 4.0 mole equivalent as sugar or sugar alcohol, to the sodium salt of said component 1).

19. The pharmaceutical composition according to claim 18, which further comprises sodium p-toluenesulfonate of 0.25 to 2.5 mole equivalent, and of sodium sulfate of 0.05 to 2.0 mole equivalent, to the sodium salt of said component 1).

20. The pharmaceutical composition according to claim 16, wherein an increased amount of a compound represented by formula (III):

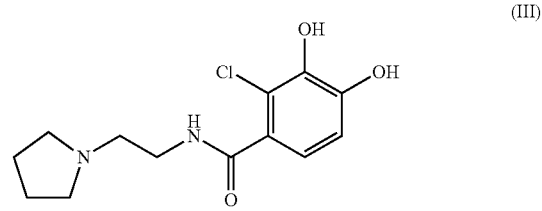

(III)

in said pharmaceutical composition is less than 0.4% from starting of storage at 40° C. for two weeks.

21. The pharmaceutical composition according to claim 16, wherein the increased amount of the compound represented by formula (III) in said pharmaceutical composition is less than 0.05% from starting of storage at 25° C. for two weeks.

22. The pharmaceutical composition according to claim 16, wherein an increased amount of a compound represented by formula (IV):

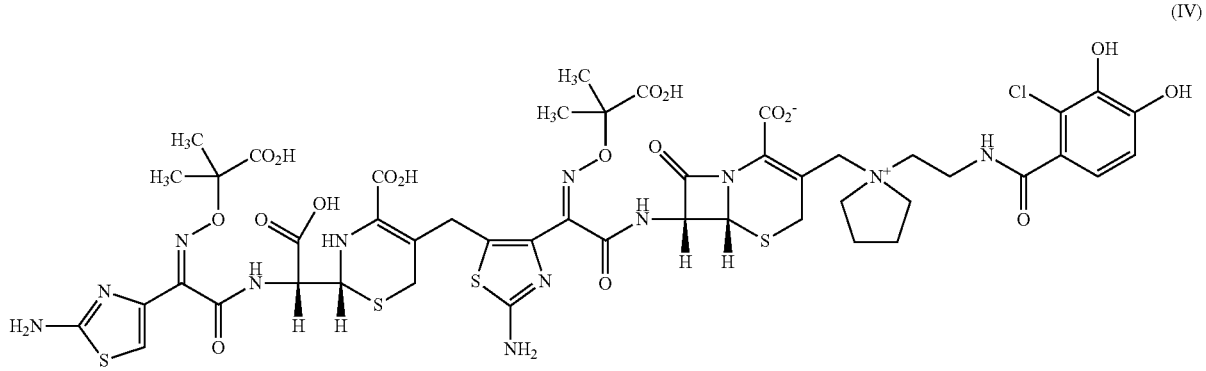

(IV)

in said pharmaceutical composition is less than 0.05% from starting of storage at 25° C. for two weeks.

23. The pharmaceutical composition according to claim 21, wherein an increased amount of a compound represented by formula (IV)

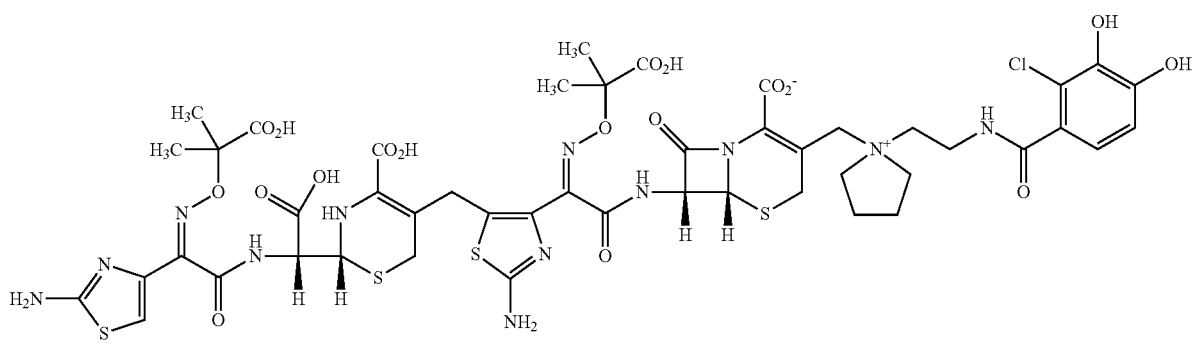

(IV)

in said pharmaceutical composition is less than 0.05% from starting of storage at 25° C. for two weeks.

24. The pharmaceutical composition according to claim 1, which further comprises sodium gluconate.

25. A pharmaceutical composition comprising:
component 1) a compound of formula (I):

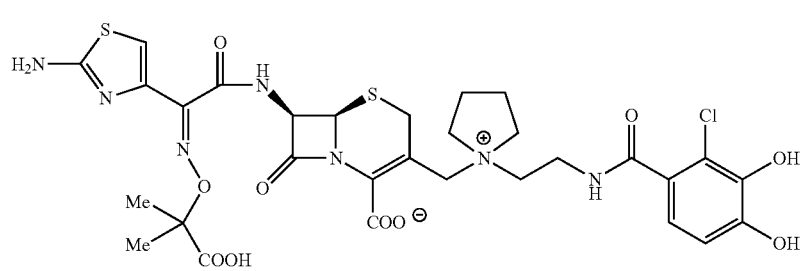

(I)

and its pharmaceutically acceptable salt or solvate thereof,
wherein an increased amount of a compound represented by formula (III):

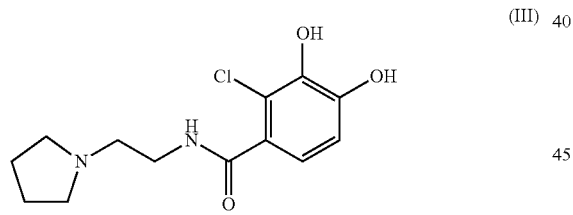

(III)

in said pharmaceutical composition is less than 0.4% from starting of storage at 40° C. for two weeks.

26. A pharmaceutical composition comprising:
component 1) a compound of formula (I):

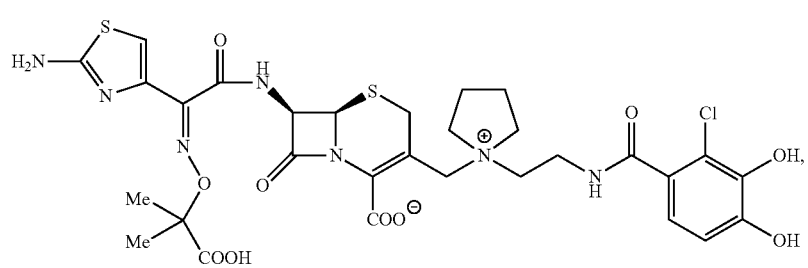

(I)

or pharmaceutically acceptable salt or solvate thereof, wherein the increased amount of the compound represented by formula (III):

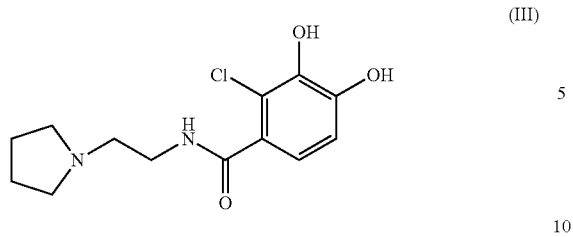

(III)

in said pharmaceutical composition is less than 0.05% from starting of storage at 25° C. for two weeks.

27. A pharmaceutical composition comprising:
component 1) a compound of formula (I):

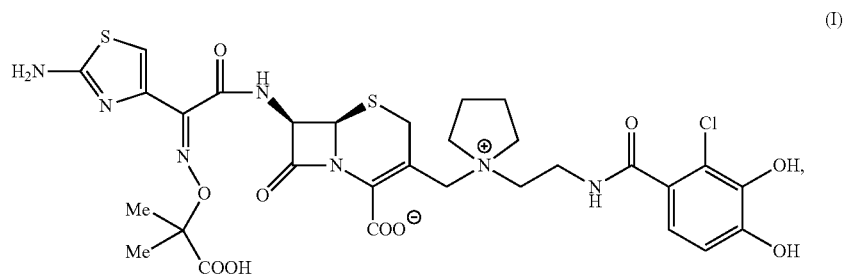

(I)

or pharmaceutically acceptable salt or solvate thereof,
wherein the increased amount of the compound represented by formula (IV):

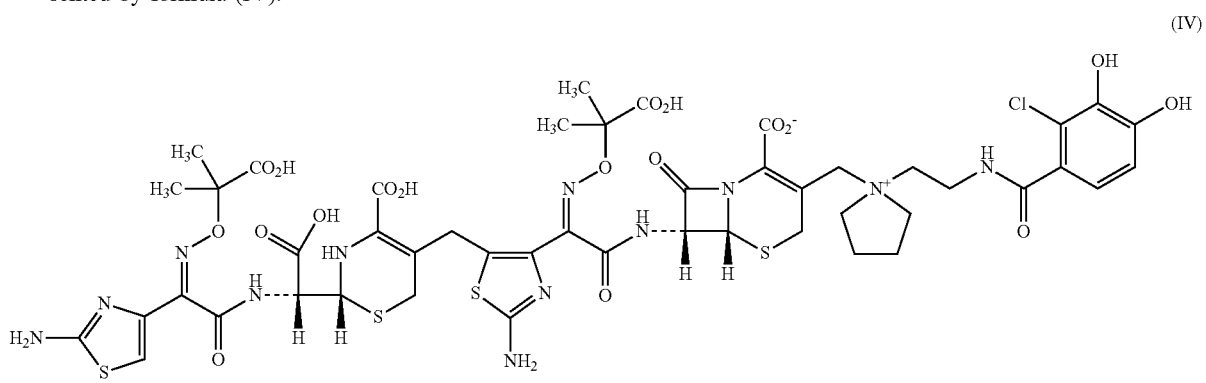

(IV)

in said pharmaceutical composition is less than 0.05% from starting of storage at 25° C. for two weeks.

28. A pharmaceutical composition comprising:
component 1) a compound of formula (I):

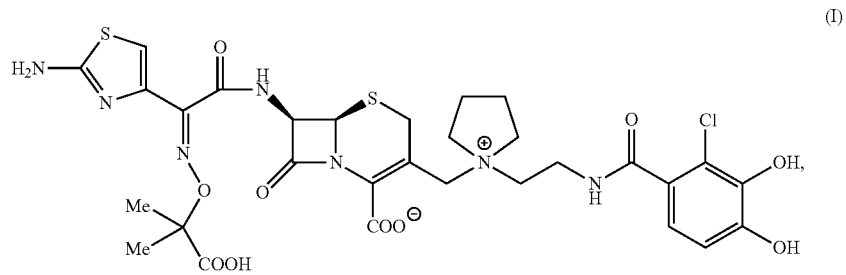

(I)

or pharmaceutically acceptable salt or solvate thereof,
wherein the increased amount of the compound represented by formula (III):

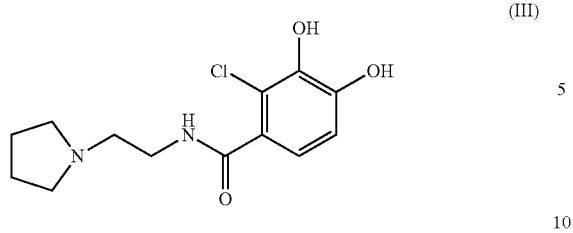

in said pharmaceutical composition is less than 0.05%, and the increased amount of the compound represented by formula (IV):

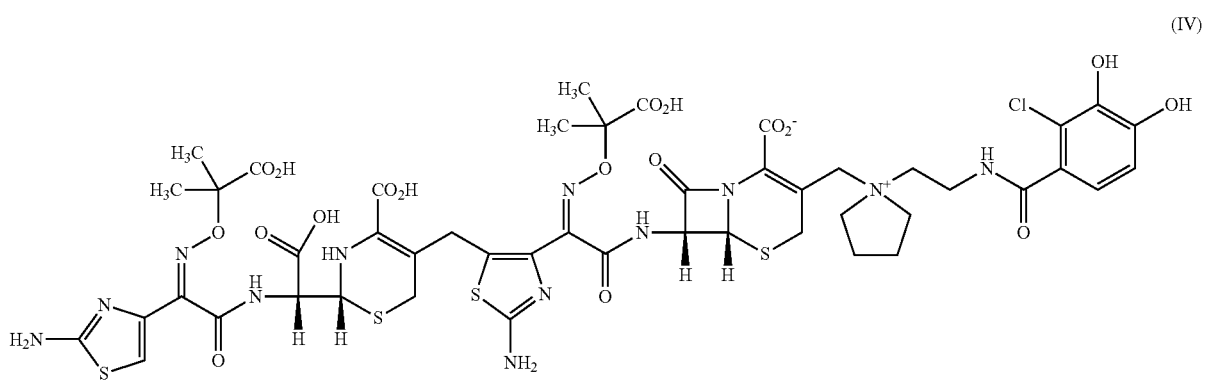

in said pharmaceutical composition is less than 0.05% from starting of storage at 25° C. for two weeks.

29. The pharmaceutical composition according to claim 1, which is a lyophilized product.

30. The pharmaceutical composition according to claim 1, which is an injectable composition.

31. A method of manufacturing a pharmaceutical preparation, comprising:
   a) a step of adjusting a pH of a liquid comprising a compound represented by formula (I):

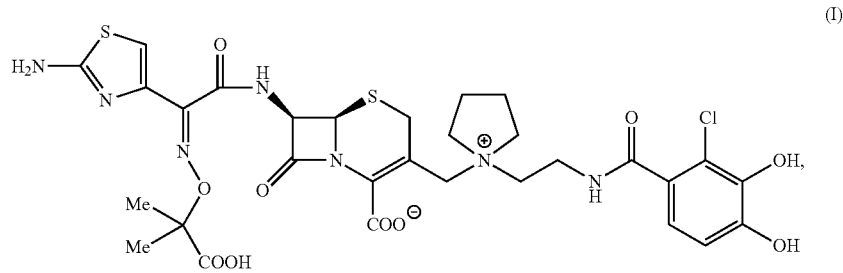

or pharmaceutically acceptable salt or a solvate thereof to pH 5 to 6 with alkali materials;
   b) a step of mixing the liquid prepared by said step a) with: one or more selected from a group consisting of alkali metal chloride, alkali earth metal chloride, transition metal chloride and magnesium chloride; and a sugar and/or a sugar alcohol; and
   c) a step of lyophilizing the mixture prepared by said step b).

32. The method of manufacturing the pharmaceutical preparation according to claim 31, wherein said alkali material is sodium hydroxide.

33. A pharmaceutical composition prepared by the method of manufacturing the pharmaceutical preparation according to claim 31.

34. A method of manufacturing a pharmaceutical preparation, comprising:
   a) a step of adjusting a pH of a suspension comprising a compound represented by formula (I):

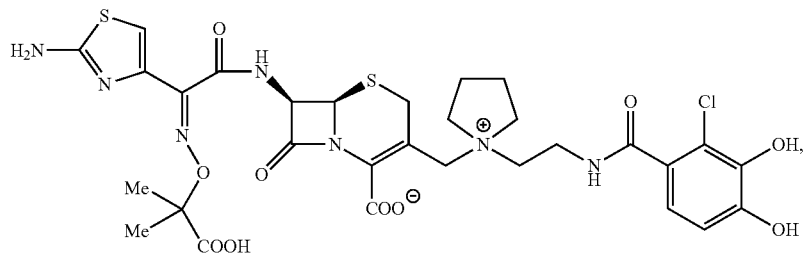

or pharmaceutically acceptable salt or a solvate thereof to pH 5 to 6 with alkali materials;
b) a step of mixing the suspension prepared by said step a) with: one or more selected from a group consisting of alkali metal chloride, alkali earth metal chloride, transition metal chloride and magnesium chloride; and a sugar and/or a sugar alcohol; and
c) a step of lyophilizing the mixture prepared by said step b).

35. The method of manufacturing the pharmaceutical preparation according to claim 34, wherein said alkali material is sodium hydroxide.

36. A pharmaceutical composition prepared by the method of manufacturing the pharmaceutical preparation according to claim 34.

* * * * *